United States Patent [19]

Weaver et al.

[11] Patent Number: 5,599,300
[45] Date of Patent: Feb. 4, 1997

[54] METHOD FOR ELECTROSURGICALLY OBTAINING ACCESS TO THE BILIARY TREE WITH AN ADJUSTABLY POSITIONABLE NEEDLE-KNIFE

[75] Inventors: George W. Weaver, East Earl; Damond C. Holsinger, New Holland; David F. Leighton, West Lawn, all of Pa.; Harold Jacob, Lawrence, N.Y.

[73] Assignee: Arrow Precision Products, Inc., Reading, Pa.

[21] Appl. No.: 440,562

[22] Filed: May 12, 1995

Related U.S. Application Data

[63] Continuation-in-part of Ser. No. 332,836, Nov. 1, 1994, which is a continuation-in-part of Ser. No. 189,317, Jan. 31, 1994, which is a continuation-in-part of Ser. No. 60,434, May 11, 1993, Pat. No. 5,397,302, which is a continuation-in-part of Ser. No. 880,842, May 11, 1992, abandoned.

[51] Int. Cl.$^6$ .................................................. A61M 31/00
[52] U.S. Cl. .................. 604/54; 604/53; 604/93; 604/164; 604/264; 128/658
[58] Field of Search .................. 604/53, 28, 93, 604/164, 264, 54; 128/654, 656–658, 4, 898; 606/39.46

[56] References Cited

U.S. PATENT DOCUMENTS 5,167,239  12/1992  Cohen et al. .
5,224,931  7/1993   Kumar .
5,336,176  8/1994   Yoon .
5,423,809  6/1995   Klicek .
5,425,705  6/1995   Evard .

*Primary Examiner*—Randall L. Green
*Assistant Examiner*—Perry E. Van Over
*Attorney, Agent, or Firm*—Amster, Rothstein & Ebenstein

[57] ABSTRACT

A method of electrosurgically obtaining access to the biliary tree of a patient and visualizing a duct thereof using a catheter having at least a first lumen and a second lumen defined therethrough, each lumnen terminating in an opening defined at a distal end of the catheter, the first lumen of the catheter having a needle-knife disposed therein and the second lumen of the catheter enabling infusion of a contrast medium to visualize the duct of the patient while the needle-knife remains in the first lumen of the catheter, the needle-knife having a distal end and being connected to a deployment mechanism at a proximal end of the catheter for extending and retracting the needle-knife between a deployed position and a fully sheathed position relative to the distal end of the catheter, the deployment mechanism having an adjustable stop for adjusting the distance between the distal end of the needle-knife and the distal end of the catheter, the needle-knife electrically communicating with a power source to enable the operator to electrosurgically incise tissue in the duct of the patient.

7 Claims, 19 Drawing Sheets

FIG. 14
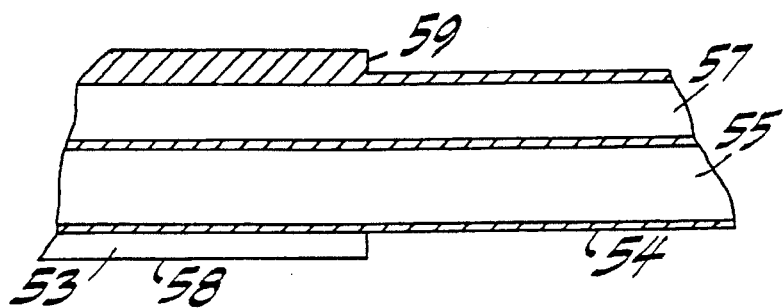
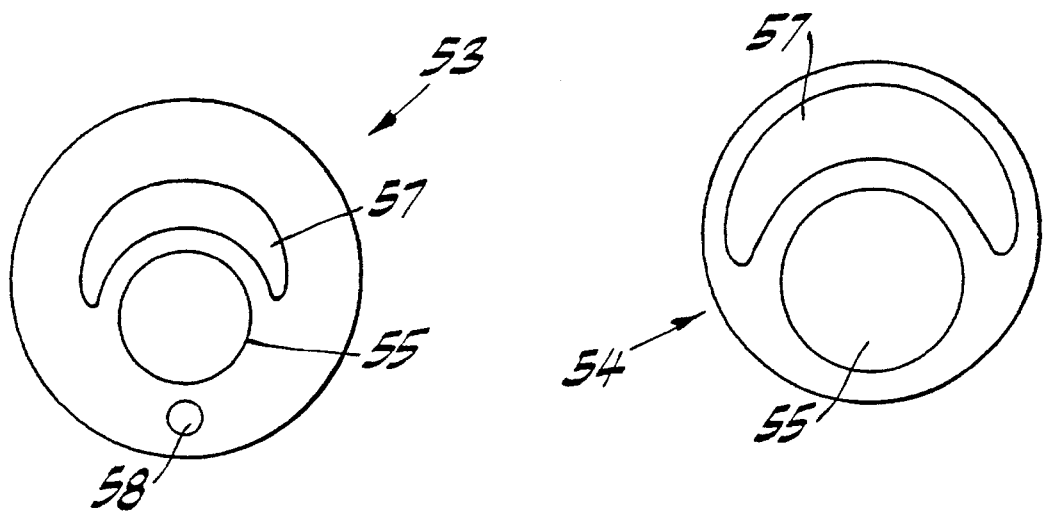
FIG. 15  FIG. 16

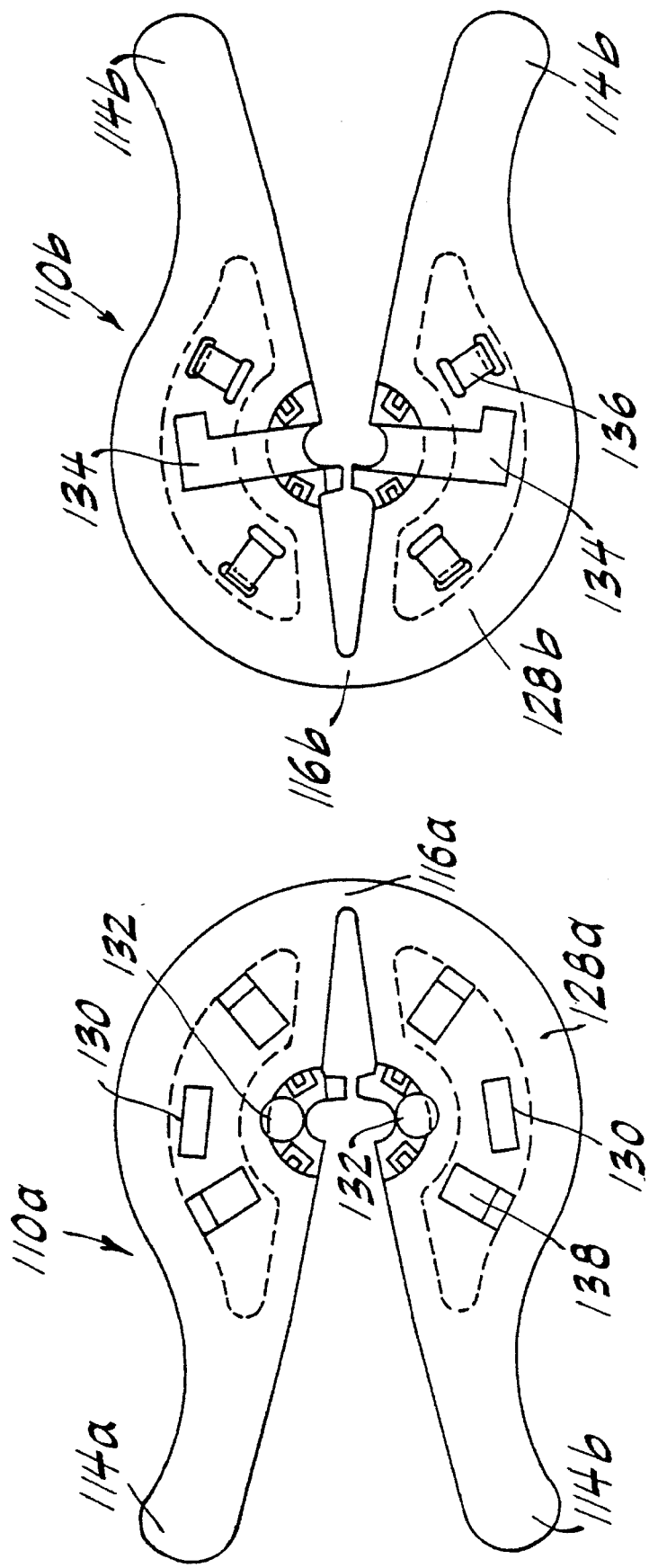

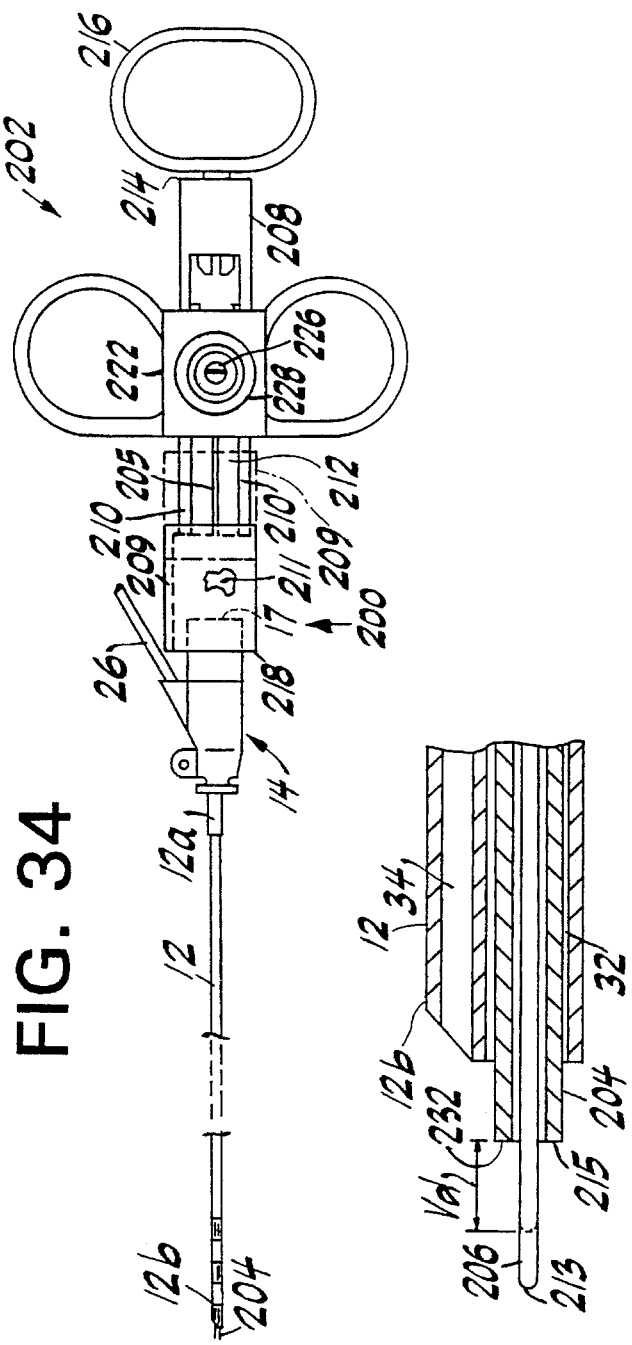
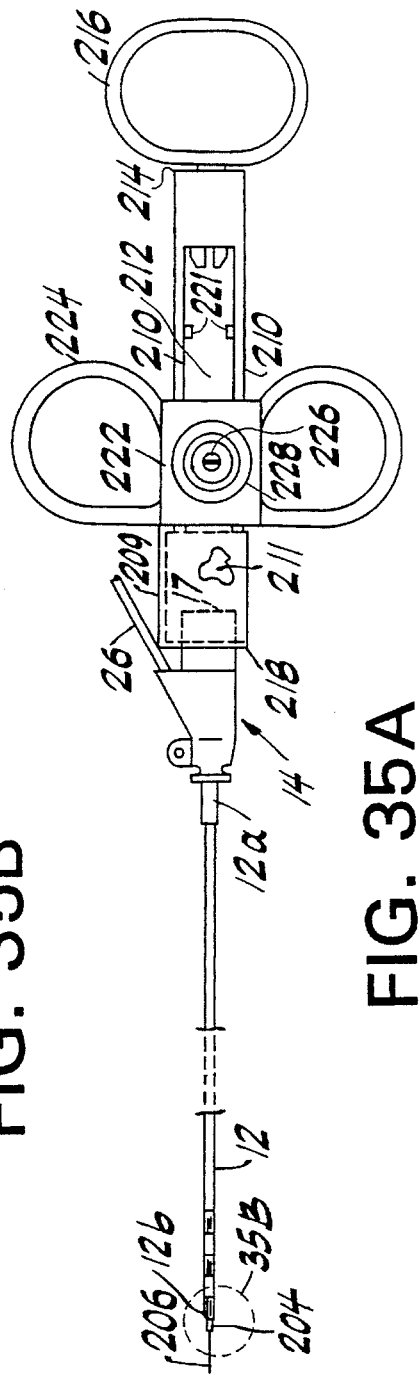
FIG. 34
FIG. 35B
FIG. 35A

METHOD FOR ELECTROSURGICALLY OBTAINING ACCESS TO THE BILIARY TREE WITH AN ADJUSTABLY POSITIONABLE NEEDLE-KNIFE

This application is a continuation-in-part of U.S. application Ser. No. 08/332,836, filed Nov. 1, 1994, which is a continuation-in-part of U.S. application Ser. No. 08/189,317, filed Jan. 31, 1994, which is a continuation-in-part of U.S. application Ser. No. 08/060,434, now U.S. Pat. No. 5,379,302 filed May 11, 1993, which is a continuation-in-part of U.S. application Ser. No. 07/880,842, filed May 11, 1992 now abandoned.

BACKGROUND

1. Field of the Invention

The present invention is directed to catheters adapted for passage through the accessory channel of an endoscope into a duct or passageway within the gastrointestinal system of the body. Although not limited in its applicability and scope, the invention has particular applicability to procedures which involve the advancement of the catheter to positions within the biliary tract and especially to the practice of Endoscopic Retrograde Cholangiopancreatography.

2. Description of the Prior Art

A number of procedures have evolved in recent years using instruments intended to be inserted through an endoscope in various positions with in the gastrointestinal system for the purpose of diagnosis and for therapeutic procedures, including the insertion of stents, devices for the extraction of stones from the biliary duct, the removal of polyps and the extraction of tissue for biopsy purposes.

One diagnostic technique which has come into use is Endoscopic Retrograde Cholangiopancreatography (ERCP) which is described in copending application Ser. No. 07/880,842, filed May 11, 1992. The ERCP technique is an endoscopic technique which involves the placement of a side-viewing instrument within the descending duodenum. The procedure eliminates the need for invasive surgical procedures for identifying biliary stones and other obstructions of the biliary and pancreatic ducts. As background of the invention, the ERCP technique exemplified the problems and difficulties which the present invention addresses.

Utilizing this technique, the Papilla of Vater and common biliary duct are cannulated, contrast medium injected and pancreatic ducts and the hepatobiliary tree visualized radiographically or examined with a duodeno fiberscope. Skilled medical practitioners can visualize approximately 90–95% of the biliary and pancreatic ducts using this technique.

ERCP is typically performed on an X-ray table. During the procedure, the patient's oropharynx is anesthetized with topical lidocaine, and the patient is sedated intravenously with diazepam. Atropine and glucagon are given intravenously to relax the duodenal muscles.

The ERCP procedure has heretofore typically been performed by the endoscopic introduction of a single lumen catheter into the pancreatic and common biliary ducts of a patient. Such ERCP catheters have typically been constructed from Teflon. At times, a spring wire guide may be placed in the lumen of the catheter to assist in cannulation of the ducts. A stylet, used to stiffen the catheter, must first be removed prior to spring wire guide insertion. The introduction of the spring wire guide eliminates the ability to inject contrast medium or makes it highly cumbersome.

To summarize the procedure, an ERCP catheter is initially inserted through the endoscope and into the biliary or pancreatic ducts. If difficulty is encountered or if the operator so desires, a spring wire guide is threaded into the catheter to assist in the cannulation. After the catheter is inserted into the duct and threaded over the spring wire guide, the spring wire guide is removed. A radio-opaque contrast medium is then injected through the single lumen of the catheter in order to identify obstructions such as bile stones. Once located and identified, such stones can then be eliminated or destroyed by methods such as mechanical lithotripsy utilizing a device such as an Olympus BML-10/20 Mechanical Lithotriptor.

This method of performing ERCP has several disadvantages. Most notably, the process of withdrawing the stylet or spring wire guide in order to clear the single lumen for contrast medium or dye infusion frequently repositions the catheter. Thus, when the radio-opaque or contrast medium is injected into the catheter, the catheter is often improperly positioned for proper fluoroscopy or X-ray visualization. Moreover, this method presents the further problem of having to repeatedly remove the stylet or an approximately six foot long spring wire guide, maintain its cleanliness and then reinsert it into the catheter. In addition, the dye is sticky and reintroduction of the guide wire is made difficult due to the frictional resistance offered by it. Finally, single lumen catheters frequently experience the problem of back-flow in which the radio-opaque dye is squirted back out the side port of the catheter and onto the administering medical professional.

The above problems often result in the need to repeat the procedure and a time consuming exercise of trial and error. Multiple attempts at properly positioning the catheter and spring wire guide are often necessary. Increased amounts of tracer dye associated with multiple injections increase the risk of pancreatitis. Because the ERCP procedure is performed under sedation, the additional time required for proper catheter positioning tends to increase the risk to the patient. Furthermore, because of the considerable expense of maintaining a procedure room, the use of single lumen ERCP catheters can add considerably to the expense of the procedure. Accordingly, practice of ERCP procedures has heretofore been limited to only the most skilled endoscopists.

SUMMARY OF THE INVENTION

The invention has particular applicability in the performing of ERCP procedures, other diagnostic and surgical procedures performed within the biliary system, as well as other parts of the gastrointestinal system in general, by the use in such procedures of catheters having at least two lumens, and preferably three or four lumens. The multi-lumen catheter assemblies of the invention are specially designed to be inserted into a duct or body passage through the accessory channel of an endoscopic instrument. A catheter assembly for use in carrying out the invention comprises, in its broadest aspects, a catheter body of substantially cylindrical shape and substantially uniform diameter having a plurality of independent lumens extending lengthwise thereof. At least two lumens exit at the distal tip of the catheter body with each exit port facing generally distally along the passage being explored axially and forwardly. The catheters of the present invention are sized to be passed through the accessory port of a conventional endoscopic instrument. The catheters have a combined length sufficient to extend the length of the standard accessory channel and into the more remote portions of the duct or passage and further have a proximal section extending proximally of the endoscope channel for a sufficient distance to allow for manipulation of the catheter by the user into the most extreme position. In the exemplary case of the biliary system, the invention allows for substantially complete exploration and visualization without the need to remove the spring wire guide. Follow-up procedures, such as stent placement, tissue sampling, use of a papillotome/sphincterotome or the like are accomplished through a lumen of the catheter already placed and may be accompanied by periodic dye injection and visualization without removal of the catheter. For certain of these procedures, the wire guide is preferably left in place, as will be noted in the explanation which follows. A further advantageous embodiment of the invention involves a multi-lumen catheter with a reduced diameter distal tip portion on which a dilatation balloon is secured. In a related embodiment, a reduced diameter distal end portion serves as a platform for a stent. Alternatively, a stent may be advanced over a catheter after performing the ERCP procedure by severing the ERCP catheter with a catheter cutter and then advancing the stent over the ERCP catheter with a second catheter. Yet another embodiment employs a needle-knife assembly which may be used in an ERCP procedure to facilitate easier access to the common bile duct.

The use of multi-lumen catheters for procedures such as described above offers many advantages over the prior art practice of using single-lumen catheters. As noted above, one important advantage is the facility for injection of contrast medium so as to attain complete visualization of a system of passages, such as the biliary tract, without the need to remove the spring wire guide. When one recognizes that a catheter for use in ERCP procedures must be approximately 200 cm in length and the spring wire guide must be an additional 200 cm or so in length, the very act of removal of the spring wire guide to allow for injection of contrast medium through a single-lumen catheter can be seen to be both awkward and time consuming. Since the spring wide guide is needed again for repositioning the catheter, its extreme length and resilient nature makes it very difficult to avoid loss of sterility when it is temporarily removed from the catheter. Furthermore, when the spring wire guide is reinserted after injection of the contrast medium through the single lumen, it has been found that because the contrast medium tends to be sticky, the resistance offered within the lumen impedes reintroduction. This condition is aggravated due to the relatively small diameter and the length of the lumen through which the spring wire guide must be passed. Since the catheters can be properly placed much more easily with less trial and error, the provision of separate lumens for dye injection and guide wire placement has been found to dramatically reduce the use of tracer dye. In addition, the provision of a separate lumen for guide wire placement eliminates the risk that air will enter the biliary tract as may occur when a single lumen is used for dye and guide wire. Still further, it is highly desirable to have further lumens within the catheter to allow for other procedures, such as the introduction and removal of stents, the use of instruments, such as papillotomes, biopsy cutters, stone extractors, forceps, knives and the like. Accordingly, it is an important objective of the invention to provide a multi-lumen catheter of small enough diameter to pass through the accessory channel of the endoscopic instrument having the following characteristics: to provide for additional lumens sized to permit the aforementioned procedures within the limited cross-section available; to retain the requisite flexibility so as to facilitate passage to a final position within an extended tortuous passageway; and to maintain the patency of the lumens without bunching up or kinking as the catheter is advanced over the spring wire guide and into a final position.

One aspect of the invention is the provision of a catheter constructed from a blend of resins producing a catheter body having peak stress of at least 8000 psi and a torqueability of at least 0.3 inch ounce at body temperature, wherein torqueability is measured as resistance to twisting through 360° with one end of the catheter fixed. An important feature of the present invention involves the treatment of at least the distal end section of the catheter with a hydrophilic coating. The hydrophilic coating of the present invention provides a highly lubricated surface which is activated by the presence of moisture. In the case of a biliary catheter, the biliary fluids activate the coating as it enters the biliary passage of the patient. The hydrophilic coating serves the further function of softening the catheter body so as to increase its suppleness and kink resistance and lubricity. Further, the softened distal portion is less traumatic to the tissue within the body passage. In a preferred embodiment, the lubricous hydrophilic coating is confined to that portion of the catheter liable to be inserted within the endoscope and the body passage. This facilitates initial passage of the catheter to the desired position within the passageway, since the catheter remains in a firmer state until it contacts the body fluid. Since the coating is quite slippery, its absence from the proximal end of the catheter allows the medical professional to retain a firm grip on the catheter as it is manipulated to the desired position. The lubricous hydrophilic coating may optionally also be applied within the spring wire guide lumen and other lumens provided for the insertion of instruments.

Preferably, catheters formed according to the invention are extruded, utilizing a blend of polymers comprised of nylon, especially nylon 11, and an ester linked polyetherpolyamide copolymer (PEBA). In the case of biliary catheters, catheters having two or more lumens, one of which is of sufficient diameter to allow passage of a guide wire and to allow passage of another device and the other for a dye or other injectable fluid and having an external diameter of between about 1.8 mm and about 3.8 mm can be formed by an extrusion process. These catheters, when coated with the lubricous hydrophilic coatings of the type herein referred, are extremely supple and offer a kink resistance not obtainable with prior art catheters formed of Teflon. When formed from the resin blends of the present invention, the catheter material does not exhibit the tendency to bunch up on the wire guide as the catheter is pushed through the passageway. The catheters have good "torqueability", that is to say, the tip follows the proximal end without undue twisting when the medical professional rotates the catheter during placement.

Preferably, the catheter has a central section substantially equivalent in length to the length of the accessory channel of a standard video duodenoscope, a distal section substantially equal in length to the portion of the body passage to be negotiated and a proximal section of a length sufficient to allow for manual manipulation when the distal section is in an extreme position within the body passage. At least the distal section but not the proximal section is coated with a hydrophilic coating which provides lubricity within the passage.

By providing exit ports in the distal tip of the catheter and orienting the ports in a generally axial direction, so that devices or injectable fluids exit distally of the catheter, procedures which involve the advancement of the catheter over the spring wire guide, use of a papillotome or other instrument and injection of contrast medium at successive locations along a relatively confined duct or passageway, such as the biliary duct, are facilitated. By use of at least two lumens having ports facing generally forwardly in the direction of movement of the catheter, removal of the wire guide from the catheter during other procedures can be avoided. Direct visualization devices and other instruments can be passed through one lumen while the spring wire guide remains in place in a second lumen for ongoing repositioning of the catheter as is desired by the user. Catheters according to the invention may be provided with a dilatation balloon or a supporting surface on the distal tip portion for support of a stent. Desirably, additional lumens are reserved for the injection of a tracer dye and aspiration of biliary fluid.

The ERCP procedure described herein can be made easier by using a pre-loaded needle-knife in a dual-lumen catheter in accordance with the present invention, to obtain easier access to the biliary tree. Because the entrance to the biliary tree is guarded by the sphincter muscle, it is often difficult for the physician to place the catheter into the common bile duct. Typically, an electrosurgical sphincteratome is used in this application. Sometimes, it is not possible to obtain access without exploratory surgery. The incorporation of a needle-knife into a multi-lumen catheter enables several diagnostic and therapeutic procedures to be performed with only one cannulation of the bile duct. In the preferred embodiment, the needle-knife is disposed in an elongated sheath which is removably installed in one lumen of a dual lumen catheter. The needle-knife is operably coupled to a hand-held deployment mechanism, preferably having an adjustable stop to provide for adjustably positioning a distal end of the needle-knife relative to a distal end of the sheath. This enables the physician to fine-tune the desired position of the needle knife during the procedure, even before the needle-knife is deployed from the distal end of the sheath. The physician can use the needle-knife to incise tissue proximal to the papillary orifice and then immediate cannulate and visualize the common bile duct with the catheter by introducing a contrast medium through the other lumen of the catheter. The needle-knife sheath and internally disposed needle-knife can be left in the catheter to function as a stiffening element to assist in the cannulation, or the sheath and needle-knife can be removed and a wire guide inserted in the lumen. This procedure does not require the catheter to be withdrawn from the patient and considerably reduces the time and effort necessary when compared with the prior art methods.

Another aspect of the invention relates to the use of a catheter cutter to separate the catheter from a catheter connector to facilitate placement of a stent in the biliary tree. After cannulating and visualizing the area under study in a duct of the patient, the catheter is severed from the catheter connector and a stent is then advanced over the catheter with a second catheter having at least one lumen of a sufficient diameter. The catheter cutter is generally comprised of a pair of members, each having a pair of hingedly connected tines, which members are clamped together about a pair of centrally disposed cutting blades. The catheter cutter is positioned at a proximal end of the catheter near the catheter connector and, in a manner similar to a wire cutter, hand pressure is applied to the tines of the catheter cutter to sever the catheter from the catheter hub without severing the wire guide. This method overcomes the more difficult and time consuming process of first withdrawing the catheter over the wire guide and then threading the stent over the wire guide.

In accordance with the present invention, it is an object thereof to provide multi-lumen catheters for use in gastrointestinal and other procedures.

It is a further object of the invention to provide a method for performing cannulation and visualization of a duct of a patient with a multi-lumen catheter having at least one lumen for receiving a wire guide and another lumen for injecting a contrast medium through the catheter and out of an opening in the distal tip thereof.

It is another object of the invention to provide a method of using a multi-lumen catheter as described above, having a needle-knife contained in a sheath disposed in a first lumen of the catheter for incising tissue proximal to the entrance to a duct of a patient to obtain access to the duct, where the position of a distal end of the needle-knife relative to a distal end of the sheath may be adjustably positioned by using a deployment mechanism having an adjustable stop, so that the duct can be cannulated and visualized by passing a contrast medium through a second lumen of the catheter without removing the sheath and needle-knife from the catheter.

It is still another object of the invention to provide a method of using a multi-lumen catheter having a needle-knife contained in a sheath disposed in a first lumen of the catheter for incising tissue proximal to the entrance to a duct of a patient to obtain access to the duct, where the sheath and needle-knife may be removed from the first lumen of the catheter while maintaining the catheter in position near the entrance to the duct, and a wire guide then inserted in the first lumen of the catheter to enable cannulation of the duct and visualization of the duct by infusing a contrast medium through a second lumen of the catheter while the wire guide remains in the first lumen of the catheter, and, if necessary, adjustment of the position of the distal tip of the catheter by advancing the wire guide along the duct and then advancing the catheter over the wire guide to visualize the duct at a desired location.

It is a further object of the invention to provide a catheter cutter for severing a first catheter used in an ERCP procedure from a catheter connector to enable threading of a stent over the first catheter with a second catheter to place the stent in a duct of a patient without having to withdraw and remove the first catheter over the wire guide.

In accordance with the above objects, the present invention will now be described with specific reference to the accompanying drawings.

BRIEF DESCRIPTION OF THE DRAWINGS

FIG. 14 is a detail view on an enlarged scale, in section, of a portion of the catheter of FIGS. 13A and 13B;

FIG. 15 is a sectional view on an enlarged scale taken on line 15—15 of FIG. 13A;

FIG. 16 is a sectional view on an enlarged scale taken on line 16—16 of FIG. 13A;

FIG. 28 is a side elevational view of the inside 35 of the top cutter component;

FIG. 29 is a side elevational view of the inside of the bottom cutter component;

FIG. 34 is a top plan view of a needle-knife assembly where the needle-knife sheath, connecting tube and needle-knife are disposed within a multi-lumen catheter in accordance with the present invention and the needle-knife is retracted in a sheathed position;

FIG. 35A is a top plan view thereof with the needle-knife in a deployed position;

FIG. 35B is a sectional detail view of the distal end of the catheter, catheter sheath and needle-knife in the deployed position.

DETAILED DESCRIPTION OF THE PREFERRED EMBODIMENTS

Preferred embodiments of the improved catheters of the present invention are described with reference to FIGS. 1–18, wherein unless otherwise indicated, the same numbers are utilized to denote the same or equivalent parts. For the purpose of description, the present invention will be described in the context of its use in the cannulation and visualizing of the common biliary duct of a patient pursuant to an ERCP procedure. It is to be recognized that the present invention is applicable to all ERCP procedures involving the cannulation and radiological visualization of the common biliary, pancreatic, common hepatic and cystic ducts and to related procedures, including those involving cholecystectomy, papillotomy, polypectomy and sphincteratomy, as well as biopsies, placement of stents and the use of cytology brushes.

Figure 1:
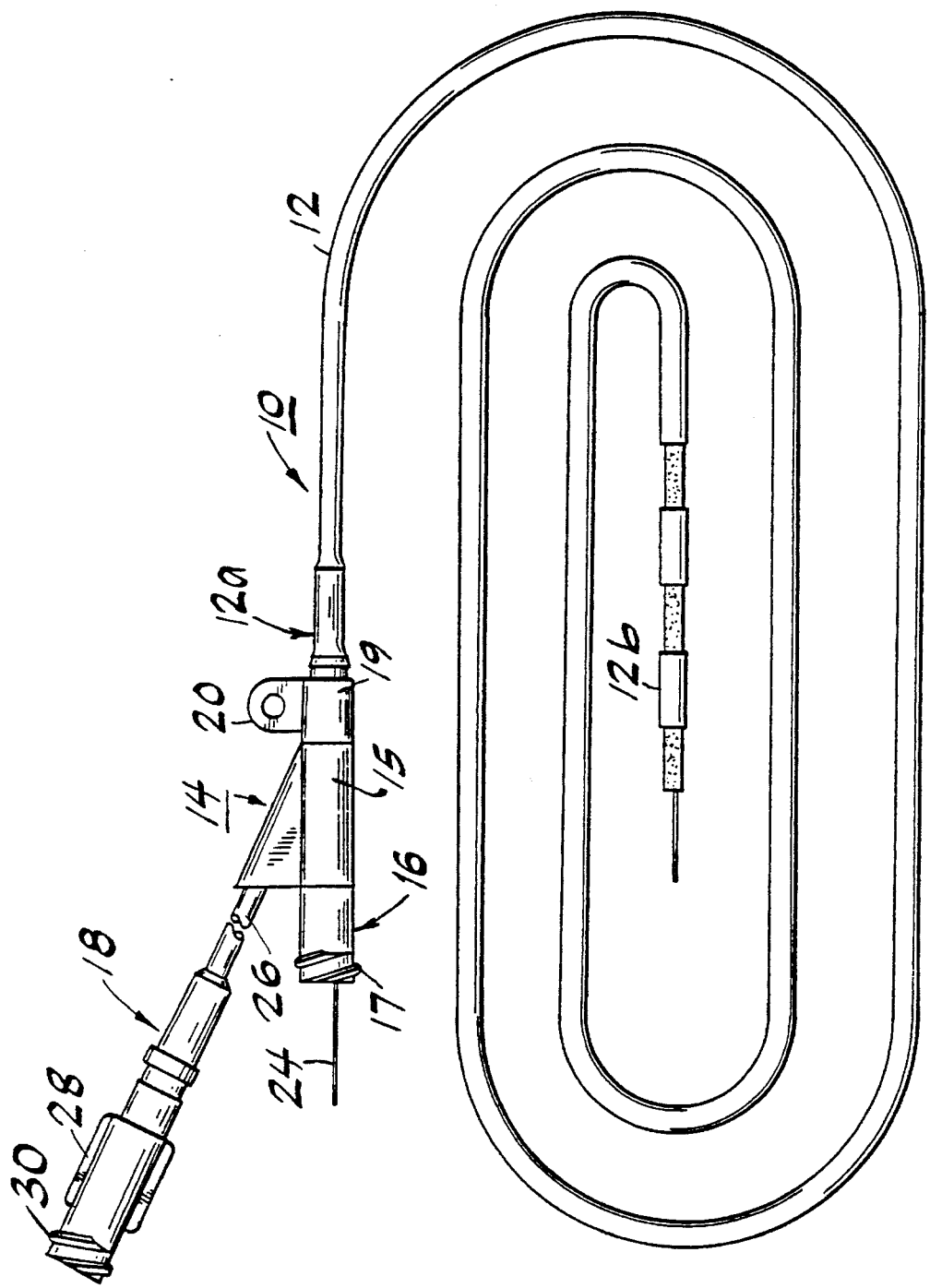
FIG. 1 is an overall view of a dual-lumen biliary catheter of the present invention.
Figure 2:
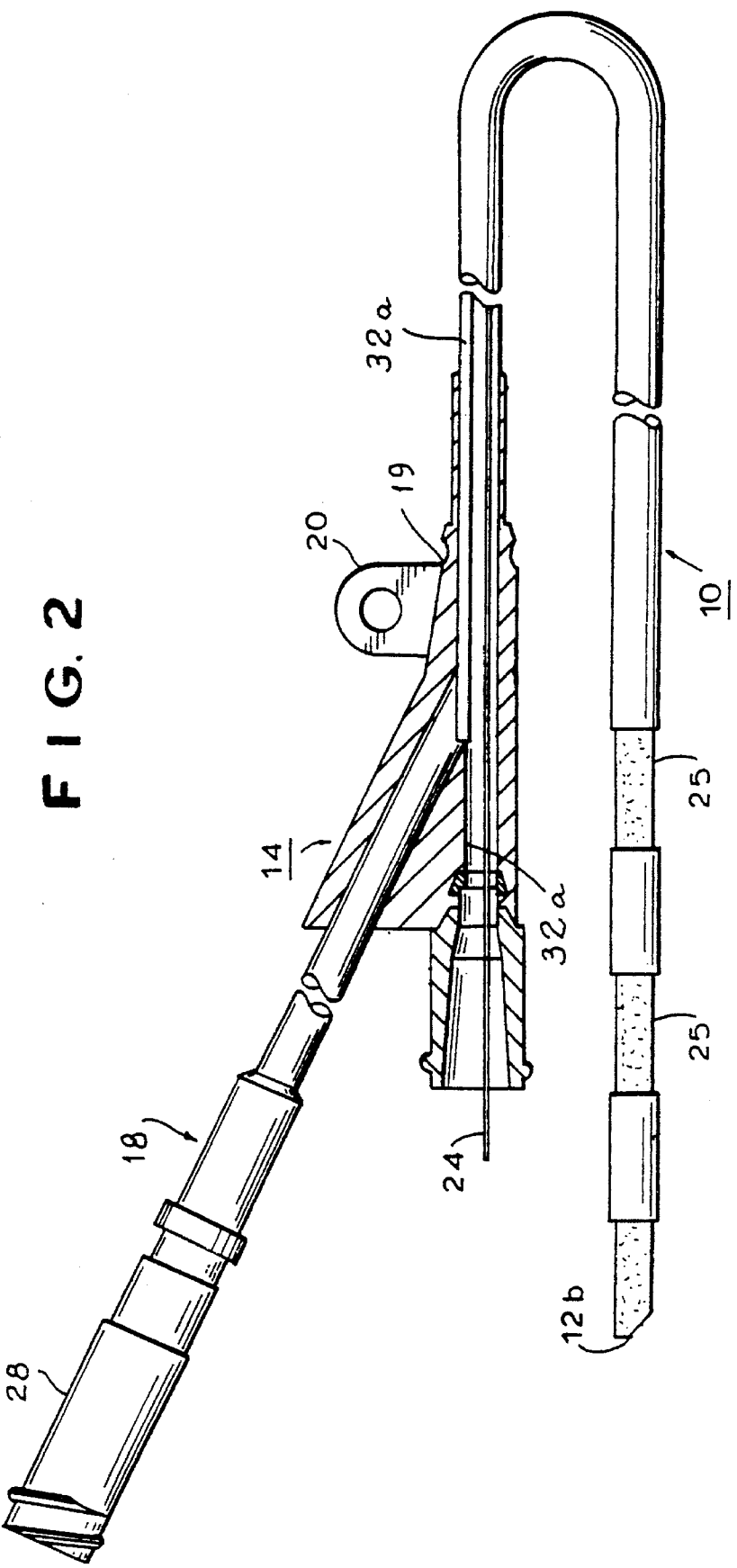
FIG. 2 is a partially broken away, partial section view on an enlarged scale as compared to FIG. 1 of a dual-lumen biliary catheter of the present invention.
Figure 3:
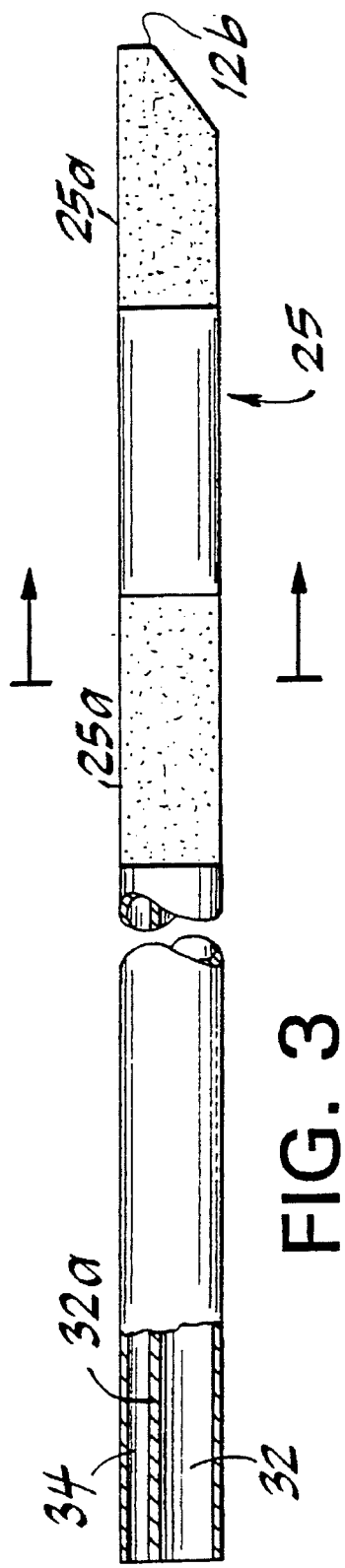
FIG. 3 is a side view, partly in section, of a dual-lumen biliary catheter body formed according to the present invention illustrating the distal tip illustrating the contrast stripes at the distal end of the catheter.

Referring generally to FIGS. 1–3, a dual-lumen biliary catheter 10, constructed in accordance with the present invention, is illustrated. In FIG. 1, showing a preferred embodiment of a dual-lumen catheter, the catheter of the present invention comprises a cannula or tubular catheter body 12 having a proximal end 12a for connection to a branching connector 14 and a distal end 12b for insertion into the biliary duct of a patient. Tubular body 12 has a substantially circular cross-sectional shape and a uniform outer diameter. Two independent lumens extend lengthwise thereof and exit through separate ports at the distal tip. Preferably, the catheter is provided with a tip having a relatively sharp bevel, although unbevelled blunt tips and conically formed tips may sometimes be employed. For reasons which will be understood from the following explanation, the two lumen ports within the tip are oriented so that they face forwardly and substantially along the path of advance of the catheter.

Tubular body 12, in a preferred embodiment of a biliary catheter, has a length of approximately 200 cm. This length is sufficient to allow the catheter 10 to be inserted endotracheally into a patient via an endoscope and to reach within the biliary and pancreatic ducts located adjacent the patient's duodenum via an attached fiberscope during an ERCP procedure.

Figure 4:
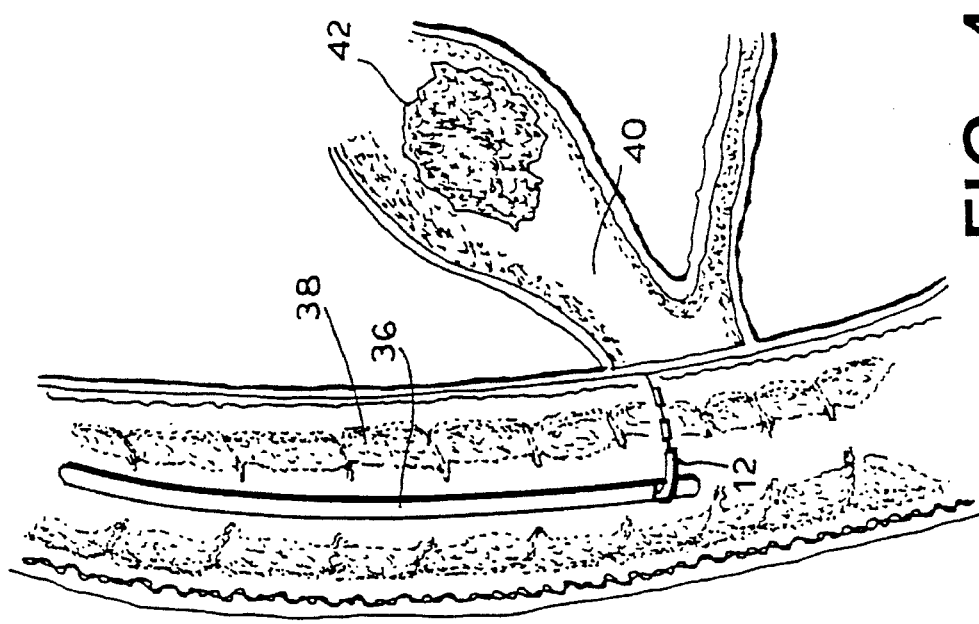
FIG. 4 illustrates a biliary catheter of the present invention through an endoscope accessory channel at the point of introduction into the common biliary duct.

The proximal end 12a of catheter body 12 attaches to branching means 14 which couples the body 12 to wire guide feeding means 16 and contrast medium infusion means 18. In a preferred embodiment as shown in FIGS. 1, 2 and 4, branching means 14 comprises a polymeric branching connector 15 which joins the wire guide feeding means 16 and contrast medium infusion means 18. The branching connector 15 may include a connector 19 having an affixed apertured wing 20.

Referring to FIGS. 1 and 2, the wire guide feeding means 16, in a preferred embodiment, comprises a port having an eighteen gauge luer lock hub 17 which is affixed to the branching connector means 14. The wire guide feeding means 16 is utilized to feed a wire guide 24 into and out of one lumen of the catheter 10. The wire guide 24 may be threaded in one lumen of the catheter 10 prior to introduction of the catheter and wire guide into the endoscope. A wire guide utilized in the embodiment of FIGS. 1–3A preferably has a diameter of about 0.035 inches. The use of a wire guide having this diameter permits the wire guide to be used for placing an indwelling stent, to be discussed below.

Figure 7:
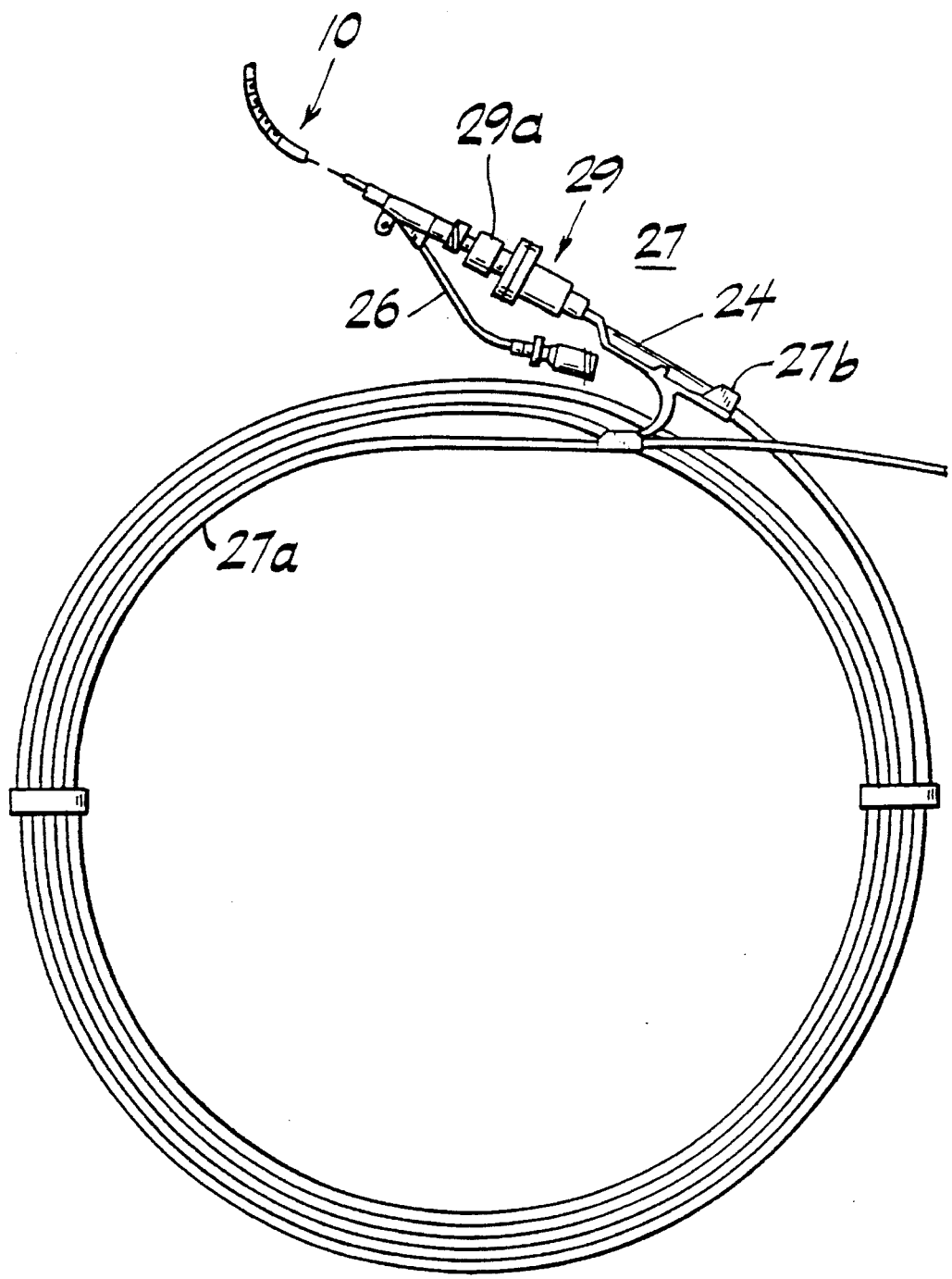
FIG. 7 illustrates the catheter and including a wire guide feed apparatus utilized with the present invention.
Figure 8:
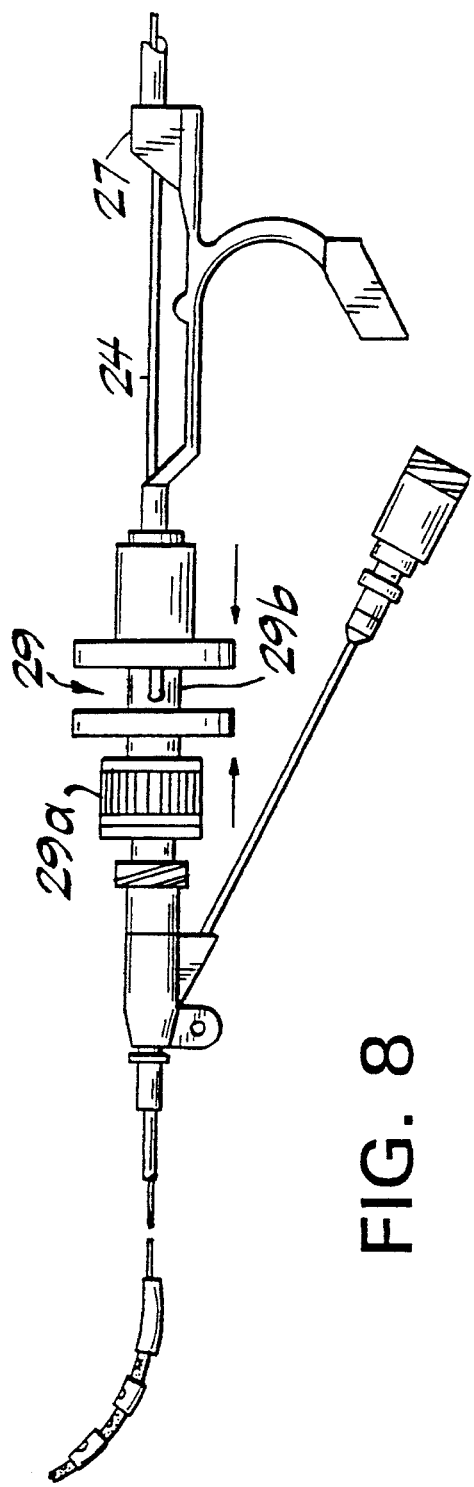
FIGS. 8 and 8A illustrate views illustrating the unlocked and locked position of a wire guide locking mechanism used with the invention.
Figure 8A:
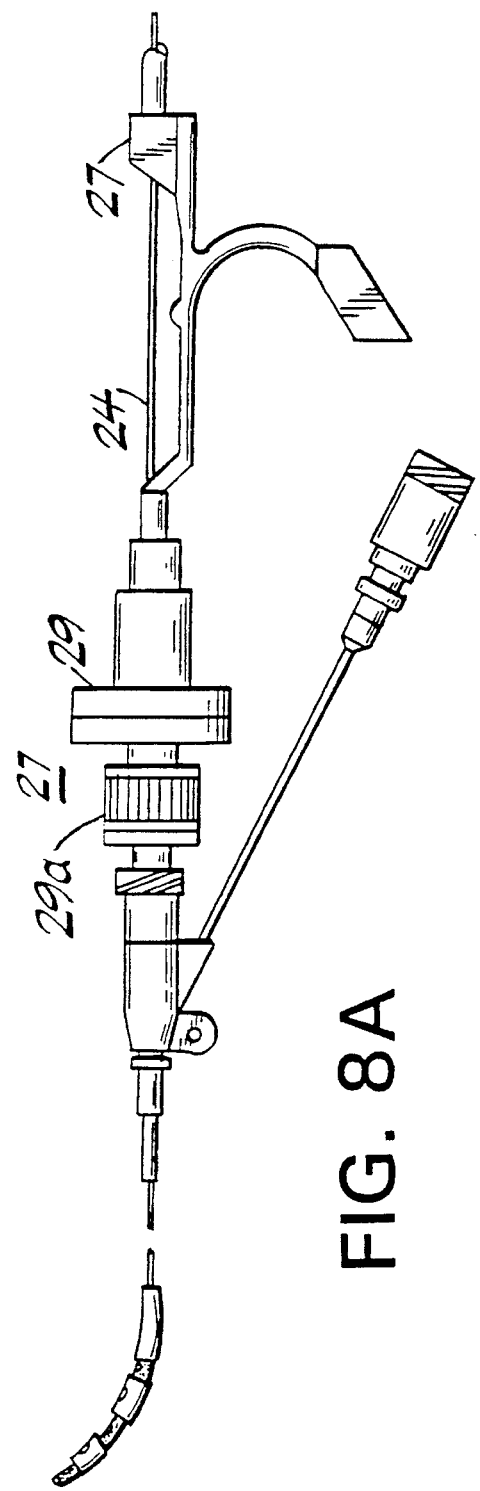

The wire guide 24 may optionally be coated with Teflon in order to add to its lubricity. The wire guide of the present invention is preferably fed and withdrawn with the assistance of an auxiliary apparatus, such as the wire guide feed apparatus disclosed in U.S. Ser. No. 07/608,234 entitled "Hand Held Device For Feeding A Spring Wire Guide", filed Nov. 2, 1990, and now U.S Pat. No. 5,125,906 assigned to Arrow International Investment Corp., assignee of the present invention, and which is incorporated herein by reference. An overall view of such a device 27 is illustrated in FIG. 7. Device 27 includes an elongated coiled conduit 27a within which the wire guide 24 resides when not in use and a feed device 27b which allows for hand feed of the wire. As shown in FIGS. 7, 8 and 8A, the wire guide feed device 27 is preferably affixed to the inlet hub of a wire clamping means, such as snap lock adapter 29 for locking the position of the wire. Snap lock adapter 29 basically comprises a knob 29a which cams a tubular portion 29b radially inwardly to grip the wire guide upon relative movement of the parts toward one another. FIGS. 8 and 8A illustrate the respective unlocked and locked positions of the adapter.

Referring to FIGS. 1 and 2, the contrast medium infusion means 18, in a preferred embodiment, preferably comprises a polymeric tube 26 which includes a twenty-gauge connector 28 secured to tube 26 at one end. The connector 28 has a threaded outer surface 30 onto which a cap or stopper (not shown) may be affixed. The interior 28a of the connector 28 is typically luer shaped and is designed to be coupled to a syringe containing radio-opaque contrast medium or dye. The contrast medium or dye is injected down tube 26 and into a contrast medium lumen 34 of the catheter, as discussed below.

Figure 9A:
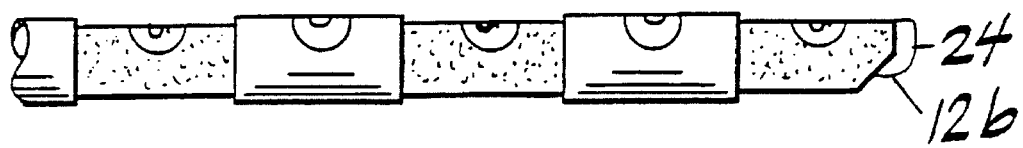
FIGS. 9A and 9B are side and top views, respectively, of a catheter of the invention having a beveled tip and digitized markings.
Figure 9B:
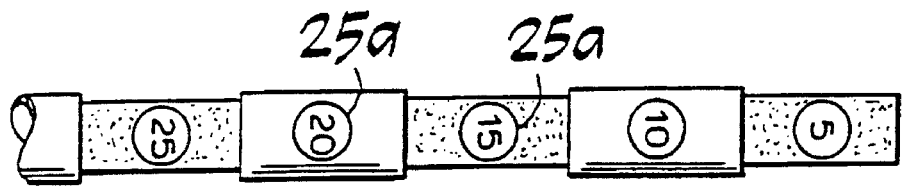

Referring to FIGS. 2 and 3, the distal end 12b of the tube 12 is shown in detail. The distal end of the catheter includes a bevelled tip portion 12b and means 25 extending proximally of the tip portion for rendering sections of contrasting the outer distal surface of catheter radio-opaque. Contrast means 25 facilitates the visual identification of the distal end of catheter 10 by the endoscope. In a preferred embodiment, means 25 comprises a plurality of non-toxic ink stripes 25a, formed using an ink such as is sold under the specification 2920 by Gem Gravure of West Hanover, Mass. It is to be appreciated that contrast stripes 25a comprising other materials may be utilized in the catheter of the present invention. Moreover, it is to be appreciated by those skilled in the art that the entire catheter 10, or portions thereof, may be or applied with any acceptable contrast medium. As shown in FIGS. 9A and 9B, the tip 12b of the catheter may be calibrated as at 25a at predetermined intervals, such as 5 mm.

As further illustrated in FIGS. 1–3, 9A and 9B, the preferred catheter tip 12b is beveled to facilitate ease of insertion and passage. A relatively steep bevel has been found to be an optimal configuration in that it is relatively easy and non-traumatic to position the catheter and affords reasonable resistance to bending and buckling.

Figure 3B:
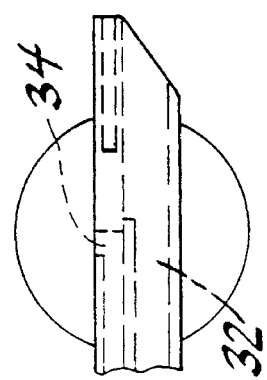
FIG. 3B is a fragmentary side view of a dual lumen catheter having a balloon at the distal tip and having the cross-sectional configuration of FIG. 3A.
Figure 3A:
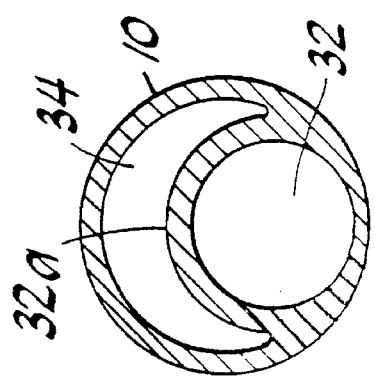
FIG. 3A is a section view illustrating the dual lumens of the biliary catheter of FIGS. 1–3 taken along line 3A—3A of FIG. 3.
Figure 10:
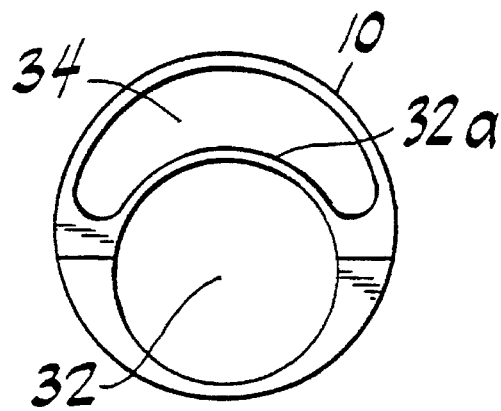
FIG. 10 is an end view of the catheter of FIGS. 9A and 9B.

Referring to FIGS. 3 and 3A, the lumens 32, 34 of a preferred form of dual-lumen catheter 10 of the present invention are shown so as to detail their cross-sectional shape. The catheter 10 includes wire guide lumen means 32 and contrast medium lumen means 34. The lumen means 32, 34 extend the entire length of the catheter body, along parallel paths between the proximal end 12a and distal end 12b. Referring to FIGS. 9A, 9B and 10, distal end 12b is shown bevelled with the contrast medium lumen means 34 terminating just distally of the wire guide lumen means 32. In all embodiments, lumens 32 and 34 exit through ports in the distal tip which are oriented so that they face generally lengthwise or axially of the catheter. As illustrated in FIGS. 9A and 10, the contrast lumen port 34 is located in the perpendicular portion of the tip, whereas the major portion of the wire guide lumen port is in the beveled position. In biliary catheters, it is preferred that the port for lumen 32 be within about one-quarter inch of the distal tip. Preferably, the dye lumen is at the tip so as to eliminate interference with dye flow by the side walls of a narrow passageway and/or by the guide wire.

As best shown in FIGS. 3A and 10, wire guide lumen means 32 is circular in cross-section and has a diameter of about 0.05 mm to allow passage of a 0.035 mm wire guide, a stent or other device of similar size. The top of wire guide lumen 32 is defined by an arcuate septum 32a which defines the interior sidewall of the contrast medium lumen 34. In a preferred dual-lumen embodiment, contrast medium lumen 34 is crescent shaped. While certain preferred embodiments of the present invention are described in the context of a biliary catheter having dual lumens, the present invention such catheters having more than two lumens. Further, while the present invention is described with respect to a contrast medium lumen 34 having a crescent shape as a means of maximizing lumen size within a relatively small diameter catheter body, certain of the objectives of the invention may be achieved when the contrast medium lumen assumes one of a plurality of other geometric shapes.

Catheters of the present invention may be constructed from extrudible polymers. Preferable proportions are about 18–22 wt. % barium sulfate, about 40 wt. % to about 60 wt % nylon 11 and about 20 wt. % to about 40 wt. % PEBA. A blend of 60 wt. % nylon 11, 20 wt. % PEBA and 20 wt. % barium sulfate is especially preferred. Nylon 11 sold under the trademark BESVOA and PEBA sold under the trademark Pebax are available from Elf Atochem, Philadelphia, Pa. The barium sulphate allows for easy visualization and catheter location under fluoroscopy and has been observed to increase stiffness. This blend is readily extruded into multi-lumen catheters having an o.d. ranging from 3.8 mm down to about 1.8 mm. Catheters formed from this blend have the requisite balance of torqueability, resistance to bunching and stretching and good flexibility.

A further important feature of the present invention is the addition of a hydrophilic coating on the outer surface of the catheter 10 and optionally within the wire guide lumen 32. The hydrophilic coating, when applied to the catheter, imparts suppleness and kink resistance to the catheter. The hydrophilic coating further apparently reduces the hardness of the polyurethane or nylon. The hydrophilic coating of the preferred embodiment comprises Methylene Chloride (MeCl), Polyethylene Oxide (PEO) and Tyrite 7617 Adhesive.

The hydrophilic coating is preferably applied to the catheter pursuant to the following process. Initially, 1400 ml of MeCl1 is poured into a container which is placed on stirrer plate. A stirring magnet is then dropped into the beaker, and the stirring plate is activated. Stirring is adjusted until a vortex forms. Next, 14.91 g.±0.02 g. of PEO are slowly added to the stirring solution. The solution is stirred continuously for about 10 minutes in order to break up any lumps of PEO. Using a syringe, about 15.75 ml Tyrite 7617 adhesive is added to the stirring solution which is stirred for an additional five minutes. The stirred solution is then poured into a treatment tank.

The catheter 10, with its end sealed offs is then dipped into the tank until the portion to be coated is immersed. The catheter 10 is left in the tank for about 1 second, quickly retrieved and the excess solution allowed to drip into the tank. The catheter is then air dried for about 8 hours.

The catheter 10 with hydrophilic coating provides a highly lubricated surface which is activated by the biliary fluids of the patient. The hydrophilic coating may also be activated by the gastric fluids which enter the endoscope. The hydrophilic coating reduces the durometer of the catheter and imparts kink resistance and suppleness to the catheter. The coating has been found to yield a lower coefficient of friction than that of comparable Teflon catheters. While the present invention is being described in the context of a preferred hydrophilic coating, it is to be appreciated that other hydrophilic coatings may be utilized in the present invention. Examples of such hydrophilic coatings are found and described in U.S. Pat. No. 4,943,460 entitled "Process for Coating Polymer Surfaces and Coated Products Produced Using Such Process." Another hydrophilic coating is Hydromer "Slippery When Wet" coating manufactured by Hydromer, Inc. of Whitehouse, N.J. Preferably, the slippery coating is not applied to the proximal end section of the catheter so as to facilitate manual manipulation thereof during catheter placement.

Figure 5:
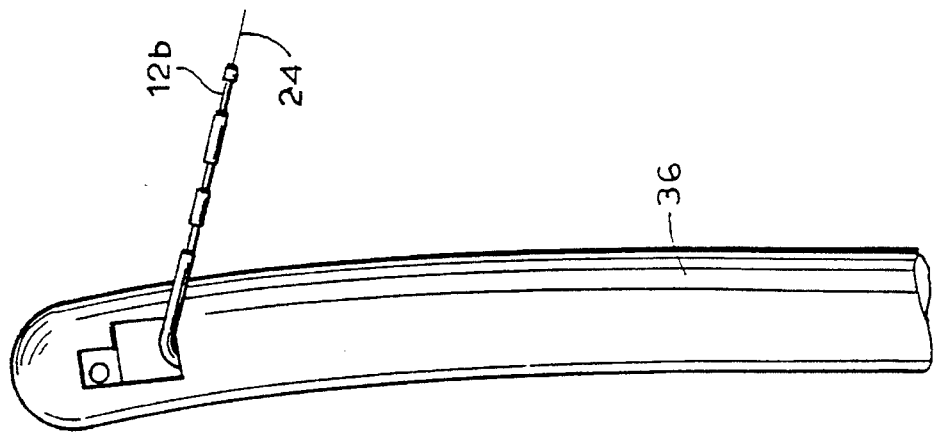
FIG. 5 is an enlarged detailed view of a catheter of the present invention illustrating its exit from the distal tip of the accessory channel of the endoscope

The operation and use of the biliary catheter 10 as so far described is now explained with reference to the Figures. Initially, the patient is sedated or, in rare situations, placed under general anesthesia. Using the wire guide advancer 27 of the type shown in FIG. 7, the wire guide 24 is inserted through an endoscope and exits through the side of an attached fiberscope 36, the end of which is shown in FIG. 5 is situated in the patient's duodenum 38 as shown in FIG. 4. The catheter 10 is then threaded over the spring wire guide 24 via spring wire guide lumen 32 or the catheter 10 having the wire guide 24 threaded therethrough is fed through the accessory channel 36 and both the catheter and wire guide are advanced into the common bile duct 40.

Next, as shown in FIG. 1, a pre-filled syringe of radio-opaque dye or contrast medium is attached to a connector 28. A sufficient amount of dye to fill the catheter is then injected into tube 26. A clamp or adhesive tape may be used to lock the relative positions of the catheter and wire guide. An example of a clamp which achieves the function is a clamp of the Series 340 clamps marketed by Halkey Medical of St. Petersburg, Fla. Contrast medium is then injected into the contrast medium lumen 34 as shown in FIG. 3A which exits at distal end 12b and into the common biliary duct 40, thereby permitting X-ray or fluoroscopic visualization of the duct 40. Markings 25a facilitate precise adjustment of the catheter. If the position of the catheter needs to be adjusted, the wire guide 24 is advanced and the catheter 10 advanced accordingly. The catheter can be rapidly adjusted and contrast medium or dye can be repeatedly infused without the need for repeated insertion and removal of the wire guide 24.

The present invention thus provides for probing with the wire guide 24 via lumen 32 and the injection of contrast medium or dye via contrast medium lumen 34, and further probing and further injection of dye until a proper catheter position is achieved. The present invention eliminates the time consuming step of removing the wire guide 24 prior to each change in catheter position and contrast medium infusion. The use of the catheter of the present invention can save over 20 minutes of time during a typical ERCP procedure. In addition, a laser fiber for biliary lithotripsy can be placed through one lumen with ongoing injection of contrast medium or fluid in the second lumen. Further, selective cannulation of the right and left hepatic ducts, cystic ducts or pancreas becomes more directed, safe and efficient.

A particular feature of the present invention is its adaptability for use in placing a stent around a biliary calculus 42 or cystic or pancreatic obstruction. In approximately 5% of all ERCP cannulations, surgery is mandated. However, surgery is often not always possible at the time of the ERCP procedure. In such situations, a stent is typically placed within the common biliary or pancreatic duct around the calculus.

As used in one procedure for stent placement, the catheter 10 is utilized in association with a wire guide 24 having a length greater than twice the length of the catheter 10, or over 400 cm in length. The wire guide may be threaded with the catheter into the endoscope, as described above. The wire guide utilized in this embodiment should preferably have a diameter of about 0.035 inches. The stent is tubular with a longitudinally extending slit which permits it to be fitted over the wire guide.

Figure 6:
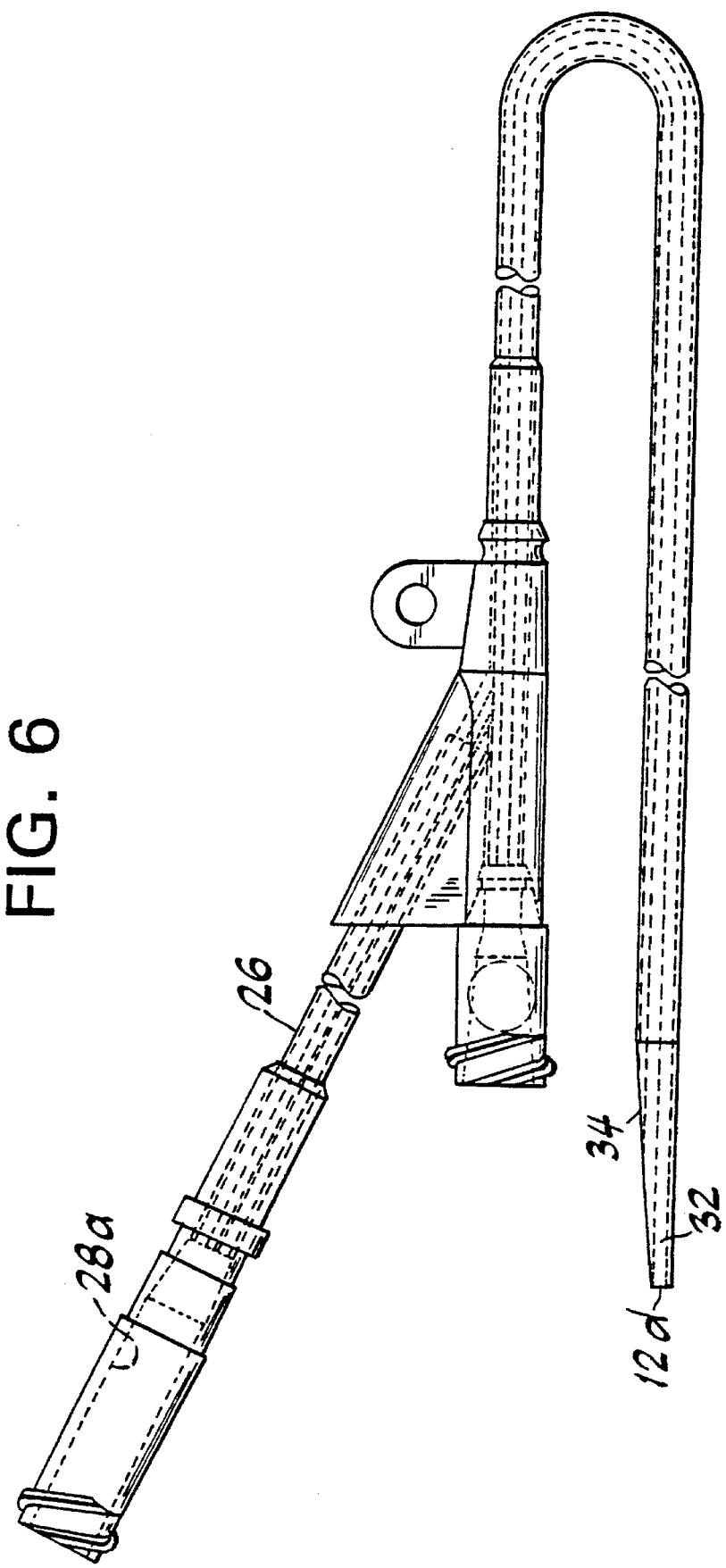
FIG. 6 is a side elevational view of an alternative distal tip configuration for the biliary catheter of the present invention.

The wire guide is advanced to a desired position within the common biliary duct and the catheter then advanced relative to the wire into a final position. Contrast medium or dye is infused, and the calculus 42 is located, as shown in FIG. 6. The catheter 10 is then removed from the endoscope.

Because the wire guide 24 has a length greater than twice that of the catheter 10, the catheter 10 can be completely removed from the endoscope over the wire guide 24 without the need for withdrawing the wire guide. After the catheter 10 is removed, a stent may be placed forward of the catheter over the wire guide. The catheter is utilized to push the stent into the endoscope, over the wire guide, into the common biliary duct and around the biliary calculus 42. When the stent is in position, the wire guide 24 is then removed along with the catheter.

Referring now to FIGS. 25–33, there is depicted an illustrative embodiment of a catheter cutter 100 for severing a catheter 12 from a connector 14 of the type described above and illustrated in detail in FIG. 1, 9A, 9B and 10 to enable a second catheter 106 to be threaded over catheter 12 to advance a stent 108 into a desired position in a duct of a patient.

Figure 26:
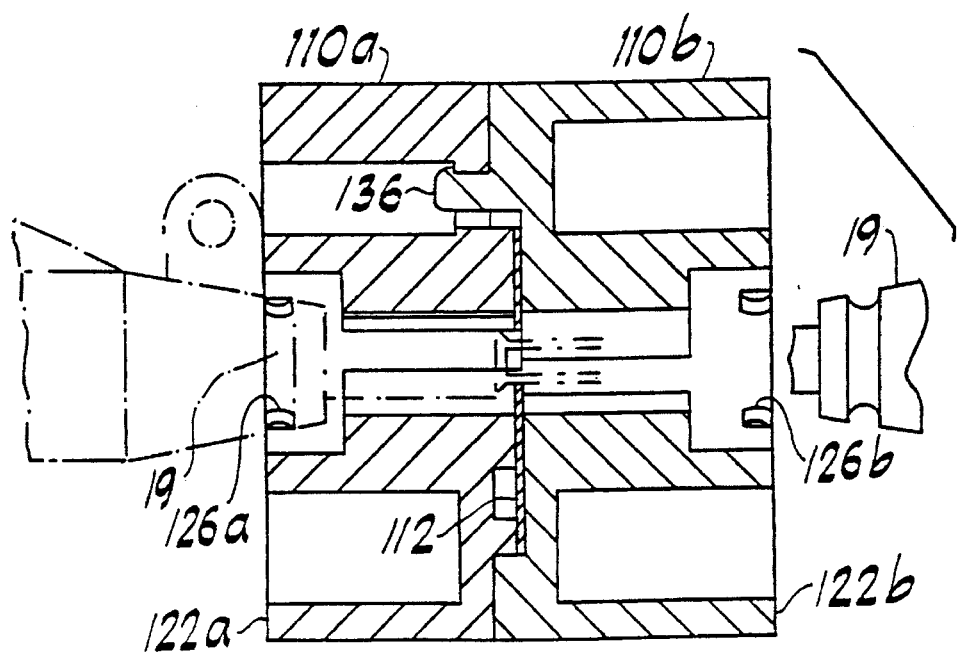
FIG. 26 is a sectional view depicting the catheter cutter assembly comprised of top and bottom components and centrally disposed cutting elements.
Figure 31:
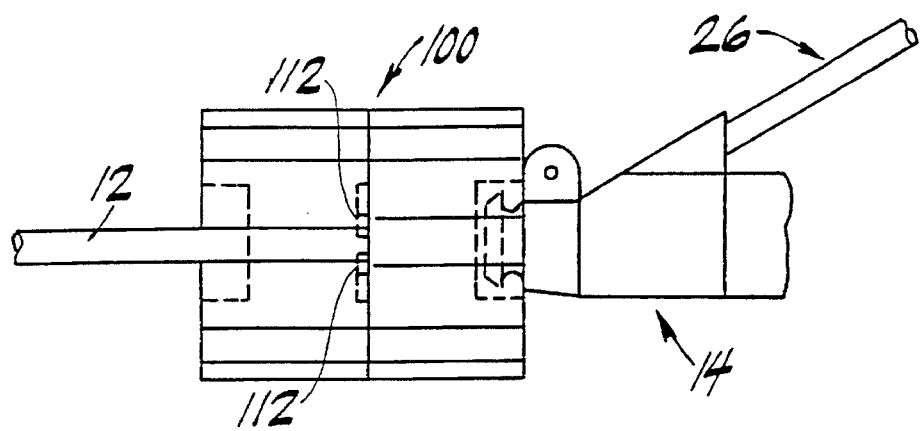
FIG. 31 is a side elevational view of the catheter and catheter connector shown in FIG. 30 with the catheter cutter disposed so as to sever a portion of the catheter to remove the catheter connector from the catheter.
Figure 32:
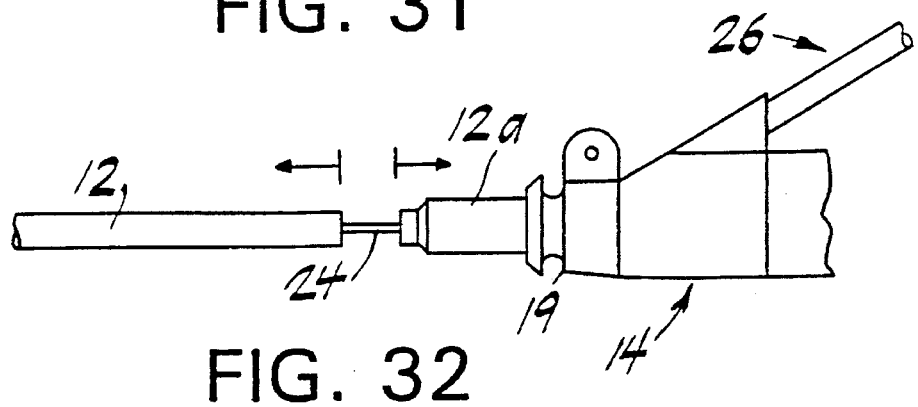
FIG. 32 is a side elevational view of the catheter being separated from the catheter connector.
Figure 33:
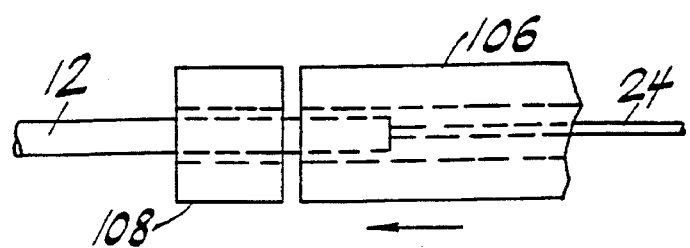
FIG. 33 is a side elevational view of a stent being threaded over the catheter with a guiding catheter placed behind the stent to advance the stent into position.

As illustrated in FIGS. 25–27 and 29, catheter cutter 100 is comprised of a top half 110a and a bottom half 110b which retain a pair of cutting blades 112 as described in more detail below. Top half 110a includes a pair of tines 114a which are hingedly connected at area 116a to enable them to flex inwardly towards one another upon the application of hand pressure. The tines 114a each define a semi-circular inner bore 118a bounded by projections 120a which engage corresponding shelves 121a to limit inward flex. At the outer end 122a of top half 110a, the semi-circular inner bore 118a of each tine communicates with a second larger semi-circular bore 124a from which a plurality of projections 126a project radially inwards to engage the flanged hub portion 19 of the connector hub 14 as illustrated in FIGS. 26 and 31. At the inner end 128a, a pair of outer bosses 130 and inner bosses 132 project for engaging the cutting blades 112 as described below. To facilitate assembly, a plurality of guideways 138 are defined inwardly from inner end 128a to facilitate assembly as shown in FIG. 26 and described below.

Figure 27:
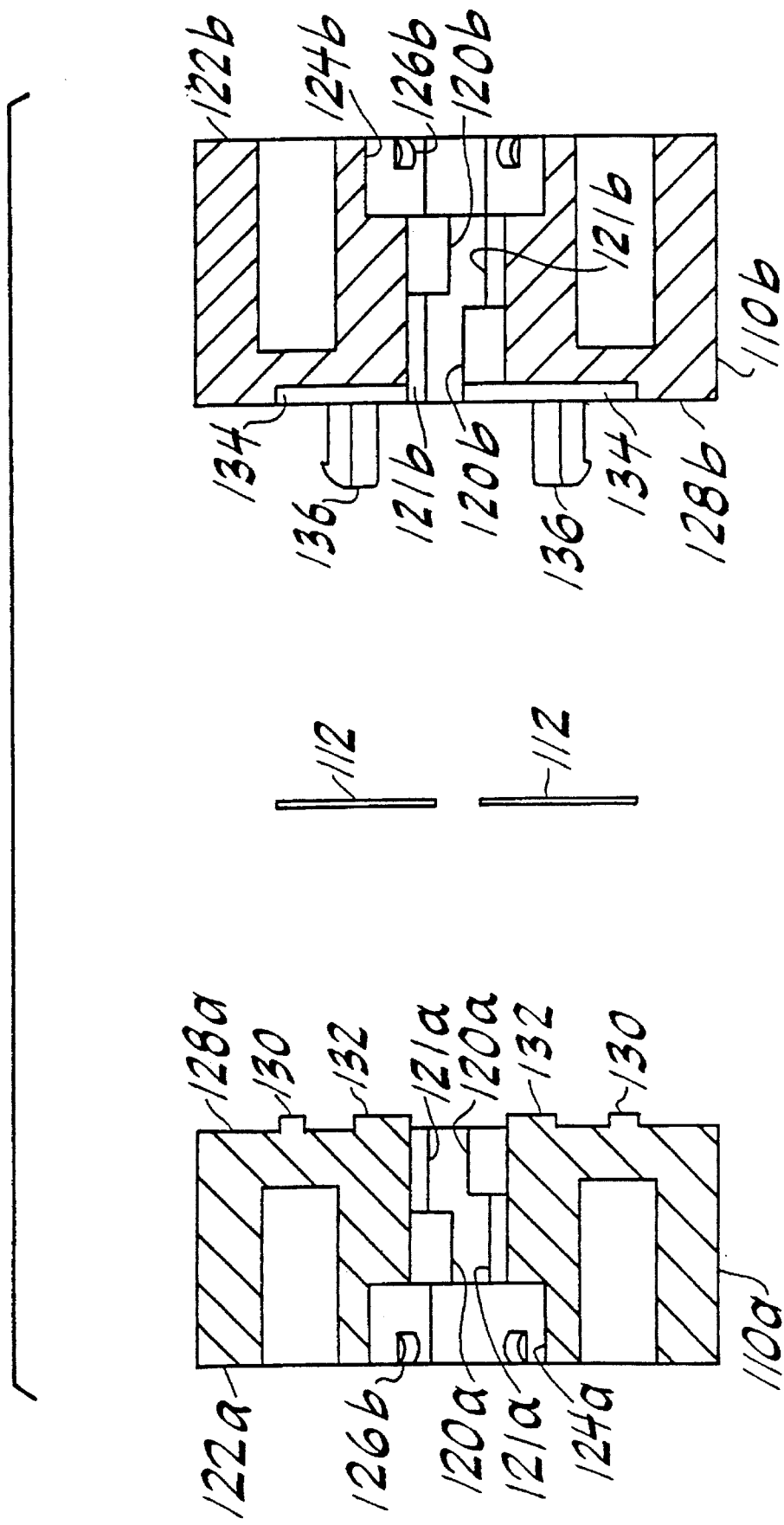
FIG. 27 is an exploded sectional view depicting the cutter top and bottom components and cutting blades prior to assembly.
Figure 30:
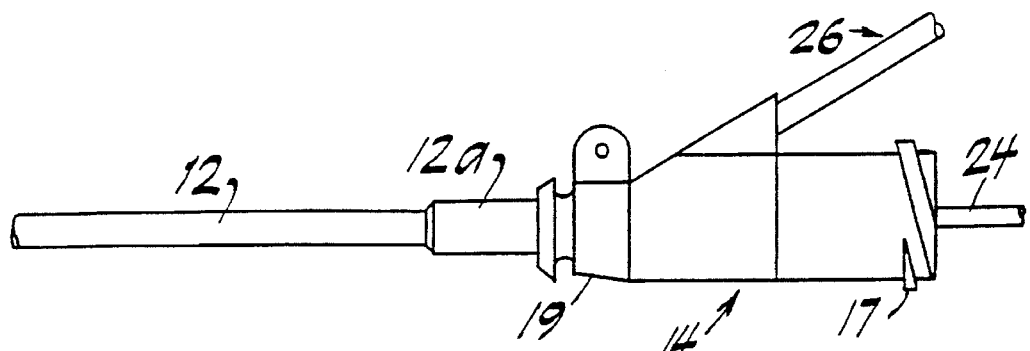
FIG. 30 is a side elevational view of a catheter and catheter connector of the type shown in FIG. 1.

The bottom half 110b is of similar construction to top half 110a, and is principally comprised of a pair of tines 114b which are hingedly connected at area 116b. The tines 114a each define a semi-circular inner bore 118b bounded by projections 120b which engage corresponding shelves 121b. At the outer end 122b of bottom half 110b, the semi-circular inner bore 118b of each tine communicates with a second larger semi-circular bore 124b from which a plurality of projections 126b project radially inwards as described above. At the inner end 128a, a pair of recesses 134 are formed, in which cutting blades 112 are disposed. The cutting blades 112 are fabricated from stainless steel and are preferably about 0.006 inches thick. The cutting blades are held in place by pressure between the top half 110a and the bottom half 110b when the components shown in the exploded view of FIG. 27 are assembled as depicted in FIG. 26. In order to facilitate assembly, the bottom half 110b includes a plurality of flexible fingers 136 which are received in guideways 138 of top half 110a in locking relation (FIG. 26).

Referring now to FIGS. 30–33, the catheter cutter 100 may be used to sever a catheter 12 from a connector 14 to enable a stent 108 to be advanced over catheter 12 without having to remove the catheter 12. The use of this procedure for stent placement as described above with respect to placing a stent around the biliary calculus, cystic obstruction or pancreatic obstruction, obviates the requirement for a wire guide having a length greater than twice the length of the catheter and the need to subsequently unthread the catheter over the wire guide 24. After performing cannulation and visualization of the duct in accordance with the procedure described above, the method entails the steps of placing the catheter cutter 12 over the flanged hub portion 19 of the connector 14 near the proximal end 12a of the catheter 12, applying hand pressure to the tines 114a and 114b until the catheter 12 is severed from the connector 14, stripping the connector 14 from the catheter 12, and then placing a stent 108 over the outer surface of the catheter and advancing the stent with a second catheter 106.

A catheter, as shown in FIGS. 3 and 3A, having a balloon adjacent its distal tip, as shown in FIG. 3B, may be used with a wire guide (not shown) having an iridium charge placed in its distal tip so as to dispose iridium for treatment in the biliary tract. In this treatment application, the wire employed is preferably 0.035 inches in thickness and is passed through a nasal passage using an endoscope. After the wire guide is positioned within the biliary tract, the endoscope is removed and the catheter is advanced over the wire guide using lumen 32 as the wire guide lumen adapted to be passed through round lumen 32 having a diameter of 0.040 inches. Lumen 34 serves as the inflation lumen and exits in a radial port for inflation of the balloon. The overall diameter of the catheter is 2.8 mm. Once the iridium, which may be fitted into the tip of the catheter at 35, is properly placed, the balloon is inflated through lumen 34 to maintain both catheter and iridium in place. Although the catheter may be deployed orally as in other procedures due to the length of the iridium treatment, the catheter is preferably inserted through a nasal passage.

Figure 11:
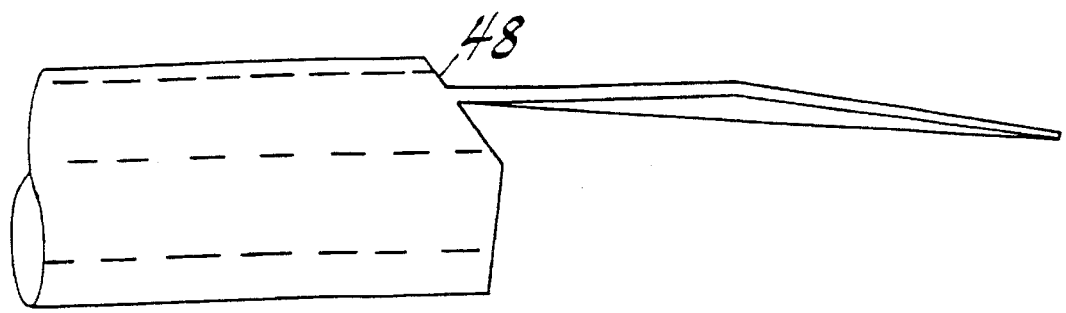
FIGS. 11 and 12 are side and end views of the distal tip section of a triple-lumen polypectomy catheter formed according to the invention.

Catheters having the cross-section of FIG. 3 are also useful for tissue sampling with a brush. In this application, lumen 32 preferably has a diameter of about 0.040 inches. Lumen 34 is utilized for a saline solution for the purpose of cleansing the tissue to be sampled prior to obtaining the sample with the brush. A triple-lumen catheter used in the practice of polypectomy is disclosed in FIGS. 11 and 12. The catheter illustrated in FIGS. 11 and 12 has a first lumen 48 dimensioned to pass a polypectomy snare, a second lumen 49 through which an injection medium will be passed and a retrieval lumen 50 for passage of a basket or other retrieval device. Lumen 49 or lumen 50 may be used to pass a flexible plastic or stainless steel needle for injecting a polyp once it is visualized to further assist the physician in excising the polyp with a snare. As indicated in FIG. 11, where a snare is illustrated projecting from the lumen port 48, the snare is a device which uses radio frequency energy to cauterize the root of the polyp and the energy so used exits through a plate in which the patient is seated. Once the polyp is incised, a net, basket or other retrieval device of known construction is passed through lumen 49 for grasping and retrieval of the polyp through the lumen. If a large polyp is to be removed, the catheter itself is removed at this point. The catheter of FIGS. 11 and 12 has an external diameter of 2.5 mm. The snare lumen has a diameter of 0.5 mm, whereas the lumens 49 and 50 have diameters of 0.4 mm. Lumen 48 exits through the bevelled portion of the distal tip, whereas lumens 49 and 50 exit through the portion disposed perpendicular to the long axis of the catheter.

Figure 12:
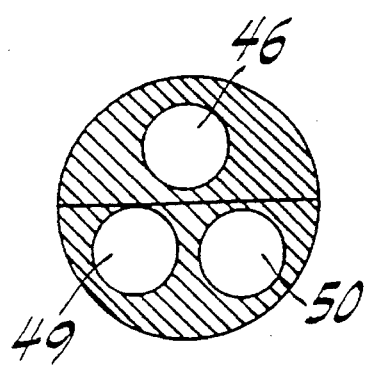
Figure 12A:
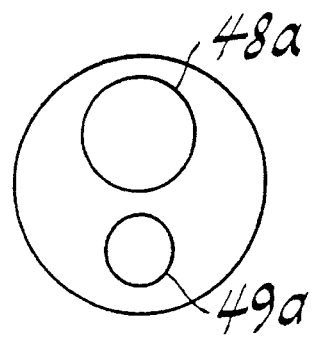
FIG. 12A is a cross-sectional view of a modified form of the polypectomy catheter illustrated in FIGS. 11 and 12.
Figure 13A:
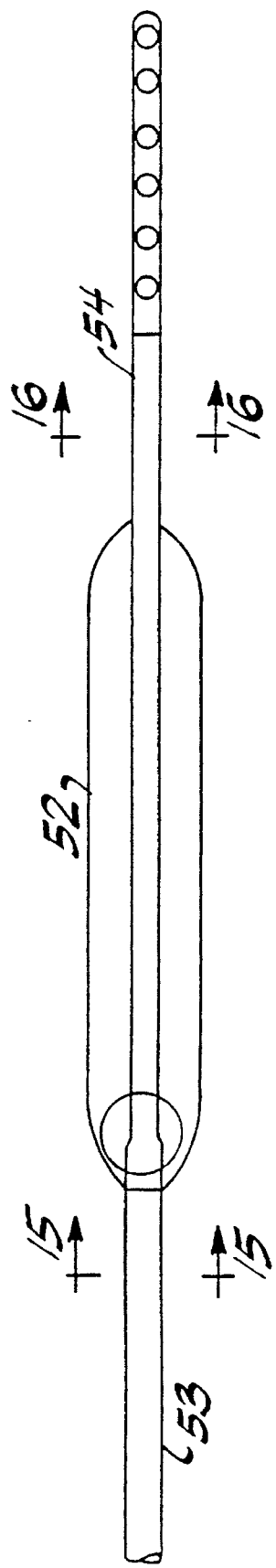
FIGS. 13A and 13B illustrate the distal and proximal end sections, respectively, of a triple-lumen dilatation balloon catheter formed according to the invention.
Figure 13B:
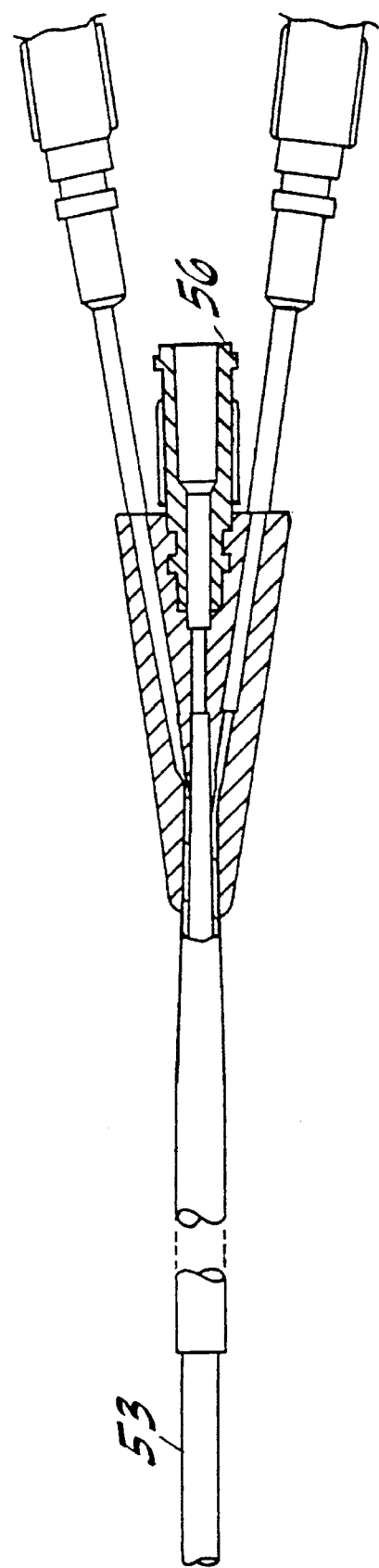

For certain purposes, the dual-lumen catheter configuration of FIG. 12A may be satisfactory for the practice of polypectomy. As utilized, the catheter configuration of FIG. 12A is provided with a lumen 48a of about 0.050 inches in diameter for passage of the snare and a lumen 49a of about 0.040 inches in diameter for the injection needle device. Retrieval is effected by withdrawal of the catheter with the embodiment of FIG. 12A. The catheter illustrated in FIG. 12A preferably has an outside diameter of about 2.8 mm.

Still another embodiment of the invention, as illustrated in FIGS. 13A–16, is a triple-lumen catheter having a dilatation balloon 52 which may be used, for example, to facilitate removal of gall stones by the dilation of a restricted portion of the biliary tract. The catheter of FIGS. 13A–16 has a main body portion 53 of a first uniform outer diameter and a distal tip portion 54 of a smaller uniform outer diameter. Preferably, the distal tip has a bevelled configuration similar to the tip of the embodiment of FIGS. 1–3.

Figure 23:
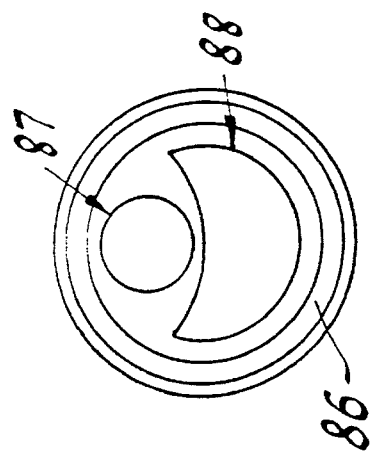
FIG. 23 is a cross-sectional view of an alternative embodiment of a catheter used for the purposes explained with respect to FIGS. 13A–16.

The catheter of FIGS. 13A–16 has a first lumen 55 which extends lengthwise thereof from a connector 56 to an exit port at the distal tip in the manner illustrated in FIG. 10. Lumen 55 is preferably sized to permit the passage of a 0.035 inch guide wire. A second crescent shaped lumen 57, as illustrated in FIGS. 15 and 16, also exits in a port at the distal tip and provides for the injection of tracer dye. The catheter is also provided with a third lumen 58 which exits in a shoulder 59 separating the larger diameter main body portion 53 from the smaller diameter tip portion 54. Lumen 58 is provided for the delivery of an inflation medium for inflating the balloon 52. The inflation medium employed is desirably an incompressible fluid and is typically a saline solution. The fluid may include a tracer dye to permit visualization of the balloon by fluoroscopy. The catheter of FIGS. 13A–16 has a maximum diameter of 2.8 mm to allow for passage through the accessory channel of an endoscope and a diameter of approximately 1.8 mm in the distal tip portion. The use of a smaller diameter distal tip portion facilitates passage into more remote portions of the biliary tract and also provides room for packing the uninflated balloon so that it does not project appreciably beyond the surface of the large diameter catheter body portion. Another catheter configuration for use with a dilation balloon 52 is shown in FIG. 23 and described below.

In use, the catheter of FIGS. 13A–16 is advanced utilizing the wire guide, as described above, until the desired position is reached, utilizing a tracer dye and fluoroscopy to assist in the guidance of the catheter to the desired location. Balloon 52 is inflated when the event a stricture in the biliary duct is encountered. Once the duct is dilated, stones encountered may, in many cases, dislodge and begin to remove themselves naturally, but if need be, a stent may be inserted to maintain patency of the duct to encourage the passage of the stone or the guide wire may be removed and an extractor device may be employed utilizing lumen 55.

Figure 17A:
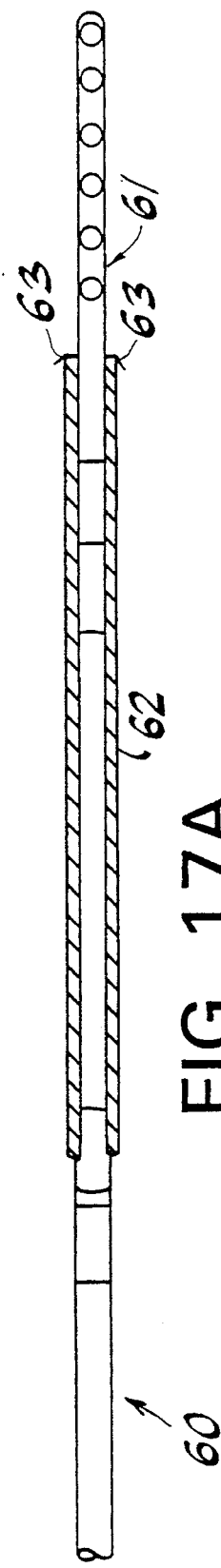
FIGS. 17A and 17B illustrate the distal and proximal end sections of a multi-lumen catheter for placing a stent.
Figure 17B:
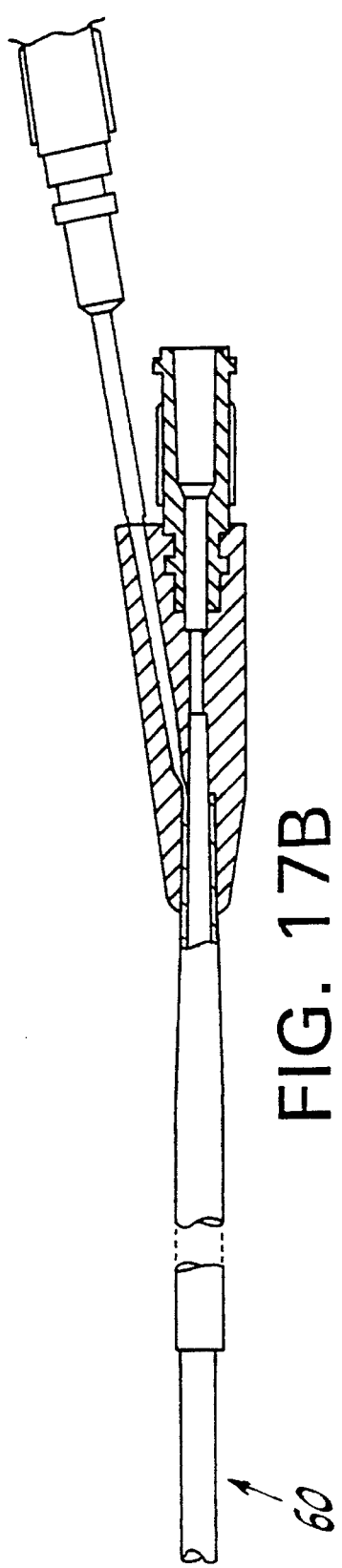
Figure 18:
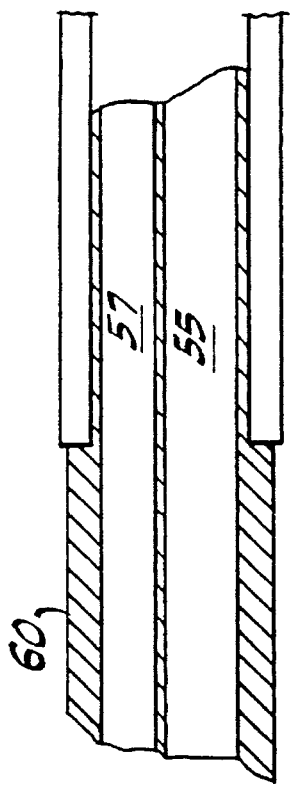
FIG. 18 is a sectional view enlarged with respect to FIGS. 17A and 17B illustrating the distal portion of the catheter with the stent in position.

FIGS. 17A–18 illustrate a catheter having utility for the placement of a stent in the biliary tract. The catheter of FIGS. 17A–18 is similar in structure to the catheter of FIGS. 13A–16 in that it has a main body portion 60 of a first diameter and a distal tip portion 61 of a second similar diameter on which a stent 62 is supported. In the illustrative embodiment, the distal portion 61 has an outer diameter of 1.8 mm which is suitable for supporting a 10 French tubular stent formed of a biologically inert material, such as polyurethane. As seen in FIG. 18, when stent 62 is placed on the distal tip portion, its proximal end surface bears against a shoulder formed between the larger diameter body portion 60 and the reduced diameter distal end portion 61. In the illustrative embodiment, main body portion 60 has an outer diameter of 2.8 mm for passage through a 3.2 mm endoscope accessory channel. The outer diameter of stent 62 is approximately 3 mm. The catheter of FIGS. 17A–18 is provided with two independent and continuous lumens 55 and 57 preferably having the configurations of the lumens in FIG. 16. Lumen 55 is dimensioned to accept a 0.035 wire guide which exits at the distal tip. The crescent shaped lumen 57 provides for the injection of tracer dye for use in visualization of the passage and location of the stricture where the stent is intended to be placed. In use, the catheter is advanced over the wire guide using the tracer dye to assist in placing it. When the stricture is located and the stent properly positioned, the catheter and wire guide are withdrawn leaving the stent in place. As is known in the art, stent 62 is provided with barbs 63 which hold the stent in position as the catheter is withdrawn. The barbs are yieldable upon application of a predetermined force by a retrieval device when it is desired to remove the stent. An advantage of the embodiment of FIGS. 17A–18 is that the relatively small diameter distal portion relatively easily negotiates restricted portions of the duct. The procedure is facilitated by maintaining the wire guide within the catheter to impart stiffness to the catheter and resistance to kinking.

Catheters having three or more lumens, as illustrated in FIGS. 11–16, allow for the performance of other procedures in conjunction with ERCP or the use of a lighting device while allowing the wire guide to remain in place. Triple-lumen catheters having outside diameters ranging from 3.8 mm down to about 1.8 mm may be extruded utilizing the resin blends described above with three lumens having inside diameters of 0.5 mm with a minimal wall thickness of 0.005 inches. One such lumen will accommodate a 0.018 mm wire guide, while the second lumen is reserved for infusion of contrast medium, and a third such lumen is reserved for additional instruments, such as a papillotome or sphincteratome, a snare, a basket and other accessories, such as forceps, stone extractor, biopsy cutters or direct visualization lighting devices. Additionally, a lumen may be provided which exits radially at a location spaced adjacent the distal tip for inflation of a dilation balloon used for dilating the tract for removing bile stones or a previously introduced stent. Catheters formed in accordance with the invention are useful for the endoscopic examination and treatment of other parts of the gastrointestinal system as well. Multi-lumen catheters can be provided with outer diameters of 3.8, 2.8 and 1.8 mm which allow for use with standard endoscopes having channels with internal diameters of 4.2, 3.2 and 2.2 mm, respectively.

An important advantage of a catheter having three or more lumens is that the wire guide may be maintained within its lumen while performing a procedure involving advancement of a device, such as a cytology brush, papillotome or an optical visualizer, allowing a third lumen to be reserved for the injection of dye. The presence of the wire guide serves to prevent kinking and collapse of all lumens, thus allowing for unimpeded advancement of the device employed, dye injection and/or aspiration of bile for laboratory analysis through a lumen not contaminated with dye. The wire guide also facilitates switching from one device to another. When using an optical device, a fourth lumen may be advantageously reserved for injection of saline solution to clear the area being visualized prior to use of the device.

Further specific embodiments and procedures of use for multi-lumen catheters formed according to the invention are described with particular reference to the cross-sectional views of FIGS. 19–24.

Figure 19:
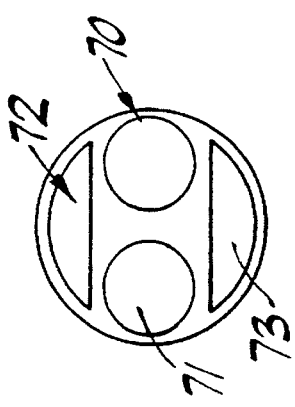
FIG. 19 is a cross-sectional view of a four-lumen catheter used for the purposes of cannulating the common bile duct and the pancreatic duct.

FIG. 19 is a cross-section of a multi-lumen catheter utilized for disposing two 0.035 inch wire guides simultaneously, one within the pancreatic duct and one through the cystic duct through lumens 70 and 71, utilizing contrast medium injected through lumens 72 and 73. Once the wire guides are in place, the catheter of FIG. 19 is withdrawn and individual catheters advanced over the selected guide wire for catheterization of either the pancreatic or cystic duct. The catheter of FIG. 19 preferably has an outer diameter of about 2.8 mm. The catheter of FIG. 19 is of advantage when an uncertainty exists as to the extent and location of patient stress.

Figure 20:
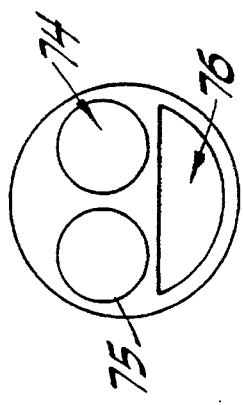
FIG. 20 is a cross-sectional view of a triple-lumen catheter in which a papillotome is accommodated for the purpose of tissue cutting as an aid to catheter insertion.

FIG. 20 illustrates a cross-section of a catheter with which a papillotome is used for tissue cutting as an aid for catheter insertion. In use of the catheter of FIG. 20, circular lumen 74 is reserved for a papillotome which is preferably permanently mounted in the lumen. Placement of the catheter of FIG. 20 involves use of additional lumen 75 for a wire guide and additional lumen 76 for contrast medium in the manner described above with respect to FIGS. 1–12. The catheter of FIG. 20 preferably has an outside diameter of about 2.8 mm.

Figure 21:
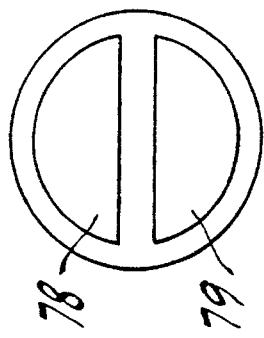
FIG. 21 illustrates a modified form of dual-lumen catheter useful for stone removal.

FIG. 21 is a cross-section of a catheter useful in procedures for stone removal. Lumen 78 (upper) is used for the passage alternatively of a guide wire or a fiber optic device for visualization of stones. Lumen 79 is reserved for passage of a stone basket. Alternatively, the catheter of FIG. 21 may be equipped with a dilatation balloon adjacent its distal tip which is inflated with an incompressible medium. After placement of the distal tip, the balloon is inflated to dilate the duct to effect dislodgment of the stone. A catheter so constructed will have an outside diameter of approximately 2.8 mm. At the option of the physician, the guide wire may be removed and replaced with the optical device for visualization of the stone removed by the basket or by dislodgment with the balloon.

An alternative use of a catheter having the configuration of FIG. 21 includes use of a vacuum assist for stone removal by application of a vacuum to one of the lumens while reserving the other either for a stone retrieval basket or as the inflation lumen for the balloon. To maximize lumen size in this application, the catheter preferably has an outside diameter of about 3.8 mm.

Figure 22:
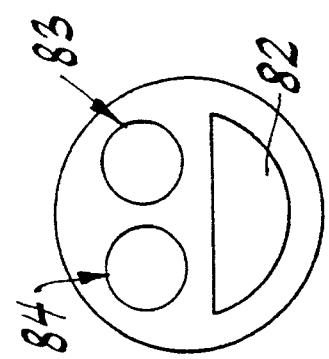
FIG. 22 is a cross-sectional view of a triple-lumen catheter used for stone visualization and removal.
Figure 25:
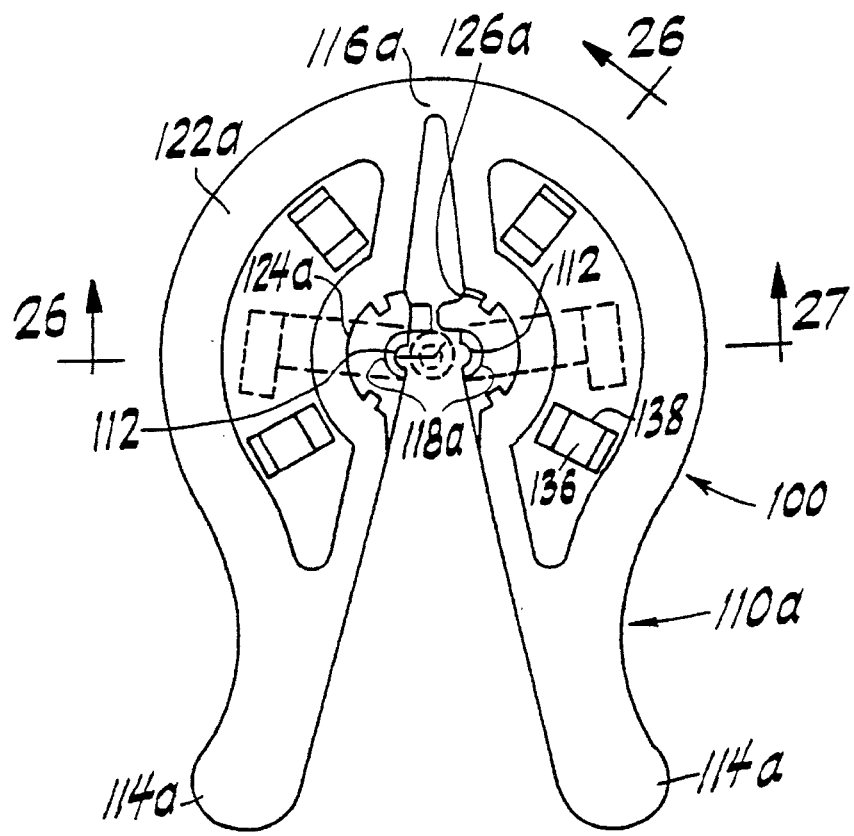
FIG. 25 is a side elevational view of a catheter cutter in accordance with the present invention.

The cross-sectional view of FIG. 22 depicts an alternative form of catheter used for visualization and removal of gall stones. As illustrated in FIG. 22, lumens 82, 83 are used for injection of contrast medium and for a guide wire respectively. Lumen 84 is reserved for a basket for the removal of stones. Once the catheter is within the biliary tract, the wire guide is removed from lumen 83 and replaced with a fiber optic visualization device to confirm that the stone, not a air bubble, is present. The basket is then manipulated through lumen 84 to retrieve the stone. The catheter of FIG. 22 has an outside diameter of about 2.8 mm.

FIG. 23 is an end view of triple-lumen catheter having an alternative configuration to the one illustrated in FIG. 15, for use with the dilation balloon 52 in which the inflation lumen, shown at 86, is an annular lumen. The annular inflation lumen 86 facilitates more rapid inflation and deflation of the balloon 52 because of the greater volume of air which may be passed therethrough as compared to the catheter configuration depicted in FIG. 15. The catheter is provided with a circular lumen 87 for a 0.035 inch wire guide and a crescent-shaped lumen 88 for injection of contrast medium. The catheter of FIG. 23 preferably has a 2.8 mm outside diameter and is in other respects substantially the same as the embodiment illustrated in FIGS. 13A–16.

Figure 24:
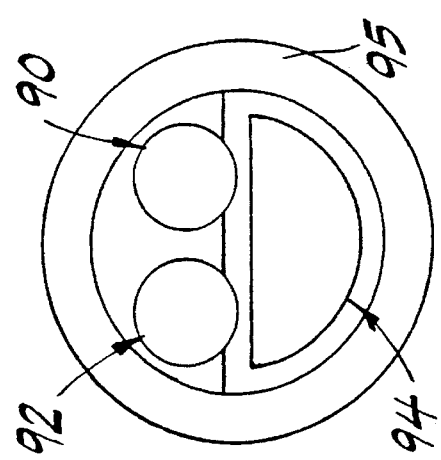
FIG. 24 is a cross-sectional view of a catheter used for stent placement and removal.

FIG. 24 illustrates an end view of a modified version of the catheter of FIGS. 17 and 18. According to FIG. 24, the catheter depicted has a wire guide lumen 90, a retrieval lumen 92 for a basket or snare and a dye lumen 94, all extending through the reduced diameter distal tip portion. Except for the inflation lumens, the lumens in FIGS. 19–24 extend continuously and independently and exit through axially facing ports. The catheter of FIG. 24 has a maximum outside diameter of about 3.8 mm. The reduced diameter distal portion has a diameter of about 2.8 mm which allows for support of a 7 French stent 95 having its circumference flush with the circumference of the remainder of the catheter. Once the stent is visualized, the snare is utilized to grasp its proximal end. The stent is withdrawn by withdrawing the snare and, if necessary, the catheter until the stent is within the large intestine where it may be released. Thereafter, the guide wire is used to locate the tip of the catheter at the desired location with the biliary or cystic duct. The catheter is withdrawn with the stent remaining in place and the catheter then removed further until it is within the intestine. The snare or basket is then used to pick up the old stent and the endoscope and catheter are then withdrawn from the body.

Figure 36:
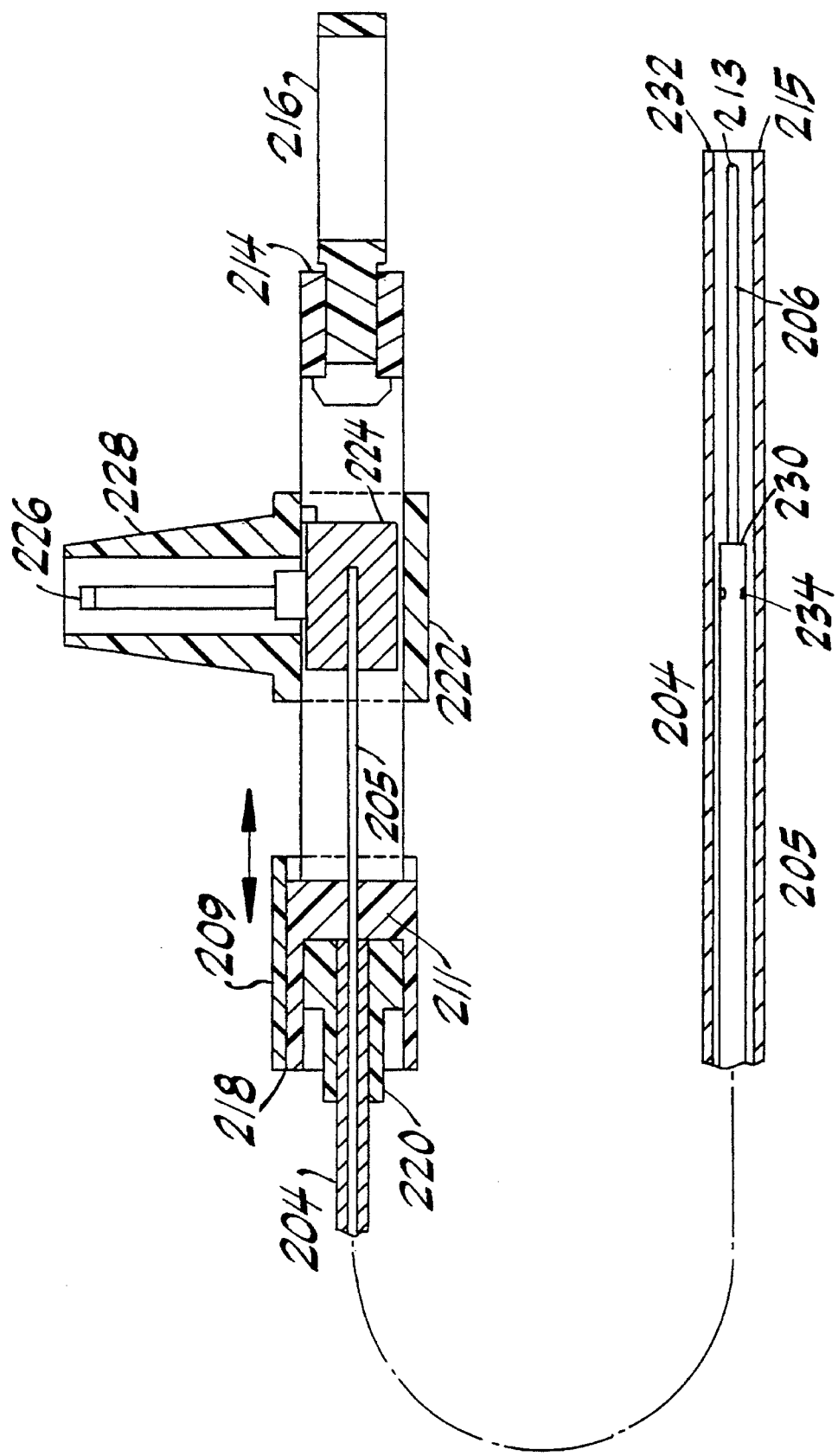
FIG. 36 is a sectional view depicting details of the needle-knife actuator assembly, sheath and connecting tube.

Referring now to FIGS. 34–36, there is depicted a needle-knife assembly 200 adapted for use with the multi-lumen catheter 12 shown in FIGS. 1, 9A, 9B and 10. The needle-knife assembly 200 is principally comprised of a deployment mechanism 202, and an elongated sheath 204 having an elongated connecting tube 205 and needle-knife 206 disposed therein.

The deployment mechanism 202 includes a body 208 having a pair of rails 210 which define a centrally disposed slot 212. Body 208 includes a first end 214 in which a thumb ring 216 is disposed, and a second end 218 having an end portion 211 at which a fitting 220 is located for receiving the sheath 204 and connecting tube 205 as described below. A sliding member 222 is slidably connected to the body 208. The sliding member 222 includes a pair of opposed finger rings 224 which enable a user to grasp the same with the forefinger and index finger. By placing a thumb through thumb ring 216, the sliding member 222 may be advanced towards the second end 218 of the body 208 to deploy the needle-knife 206, and retracted towards the first end 214 and against stops 221 to withdraw the needle-knife 206 into the sheath 204 as described below. A slidable stop 209 is disposed over the end portion 211 as shown. The sliding stop 209 may be moved towards and away from the second end 218 to limit the travel of the sliding member 222 to enable adjustable positioning of a distal end 213 of the needle-knife 206 relative to a distal end 215 of the sheath 204 by a variable distance $V_d$ between a fully deployed position (FIG. 35B) and a sheathed position (FIG. 34). The sliding member 222 has an internally disposed brass insert 224 which electrically communicates with a brass binding post 226 for making an electrical connection to a power source (not shown) to provide a cutting/coagulating current as is well known in the art. The binding post 226 is situated within a connector cap 228 integral with sliding member 222.

As shown in FIG. 36, the elongated connecting tube 205 is attached to and electrically communicates with the insert 224. The connecting tube 205 is fabricated from stainless steel and extends through the fitting 220 in the second end 218 of the mechanism body 208 and terminates in a distal end 230. The connecting tube 205 has a hollow bore (not shown) into which the needle-knife 206 is partially disposed near distal end 230. The connecting tube 205 is then crimped over the needle-knife 206 at location 234 as shown in FIG. 36. The fitting 220 tightly receives the elongated tubular sheath 204 and provides strain relief therefor. In a preferred embodiment, the sheath 204 is made from polyimide material with a Teflon coating. This enables fabrication of a sheath 204 with an outer diameter as small as approximately 0.035 inches, to enable advancing the same through one lumen of the dual lumen catheter 12 used in an ERCP procedure in accordance with the present invention. The use of polyimide material provides good kink resistance, even if the sheath is fabricated with a very thin wall thickness, and the Teflon coating provides a smooth surface to enable the sheath 204 to be easily inserted and removed from the catheter 12. FIG. 35B shows the orientation of the connecting tube 204 disposed within the catheter 12, where the distal end 232 of the sheath 204 extends a nominal distance from the distal end 12b of the catheter 12.

In the preferred embodiment, the needle-knife 206 has a diameter of approximately 0.006 inches, and is fabricated from a "memory" metal alloy such as Nitonil. As is known in the art, memory metals undergo a crystalline phase change and thermoelastically deform when heated and cooled. These crystal phase changes between what are known as high temperature Austenite and low temperature Martensite, enable a component made from such material to contract when heated, and to return to its original configuration when cooled. Moreover, the stress-strain behavior of a memory metal alloy makes the material much easier to deform when cooled (Martensite) than when at an elevated temperature (Austenite). In the present invention, the use of this material is advantageous since the needle-knife 206 is very thin and susceptible to deformation during the cutting procedure. The memory material helps it return to its original orientation if deformed by stress during the cutting procedure. When the needle-knife 204 is heated by applying the cutting/coagulating current, the crystalline transformation to Austenite makes it much more difficult to deform. If a sufficient force is then applied to the needle-knife 206 during the procedure, the material can strain to relieve the applied stress as it transforms back to Martensite, and once the stress is reduced, it will unstrain and revert back to Austenite. Finally, after the applied current is removed, the resulting cooling of the needle-knife material and associated crystal phase change to Martensite makes it more flexible.

Referring now to FIGS. 34, 35A and 35B, the needle-knife 206 is disposed so as to remain in a sheathed position within sheath 204 with respect to the distal end 232 thereof. The sheath 204 is inserted through lumen 32 of catheter 12 so that the distal end 232 of the sheath protrudes slightly beyond the distal end 12b of the catheter 12. The catheter assembly (of the type shown in FIG. 1) is attached to the deployment mechanism 202 by threading the luer lock hub 17 of the connector 14 into the insert 220 at the second end 218 of the deployment mechanism 202.

Preferably, the needle-knife assembly 200 is pre-loaded in the catheter 12. This facilitates the use of the needle-knife assembly in a typical ERCP procedure using a multi-lumen catheter. In this method, the physician advances the catheter 12 through an endoscope (as shown in FIG. 4) and into the patient's duodenum proximal to the entrance to the common bile duct 40, typically into or just above the papillary orifice. By grasping the deployment mechanism 202 by finger rings 224 and thumb ring 216, the physician then advances the sliding member 222 towards the second end 218 of the deployment mechanism 202 to cause the needle-knife 206 to extend from the distal end of the sheath 204 as shown in FIGS. 35A and 35B. As described above, the slidable stop 209 may be moved over the end portion 211 to custom position the needle-knife 206 with the distal end 213 thereof at a desired distance $V_d$ relative to the distal end 215 of the sheath 204 prior to moving the sliding member 222 towards the second end 218. The physician applies an appropriate amount of cutting/coagulating current to the needle-knife 206 through the binding post 226, and manipulates the needle-knife by using the elevator and/or positioning controls of the endoscope to incise tissue. Typically, a 3–5 millimeter across by 2–4 millimeter deep incision into the papilla is sufficient. The needle-knife 206 is then retracted into the distal end 232 of the sheath 204 by moving the sliding member 222 rearwardly towards the first end 214 and against the stops 221 of the deployment mechanism 202. This enables the physician to insert the catheter 12 into the common bile duct with less effort. Once access is gained to the common bile duct, the physician can then cannulate and visualize the same in accordance with the ERCP procedure described in the foregoing. The sheath 204 and needle-knife 206 can be left within the first lumen 32 of the catheter 12 to function as a stiffening element to enable advancing the catheter into the common bile duct 40 (see FIG. 4), or the sheath 204 and needle-knife 206 may be withdrawn from the catheter 12, and a wire guide 24 then inserted in its place by simply unthreading the luer lock hub 17 from deployment mechanism 202 and attaching a wire guide feeding apparatus 27 as shown in FIG. 7 and described above. The common bile duct 40 can then be visualized by infusing a contrast medium through lumen 34. To facilitate further cannulation and/or visualization of the common bile or other ducts, the wire guide 24 may be advanced along the duct and the catheter 12 then repositioned by advancing the catheter 12 over the wire guide to the appropriate location, and the infusion procedure may be repeated.

This method saves a considerable amount of time over prior art procedures where cutting instruments had to be removed prior to infusing the contrast medium. By keeping the needle-knife assembly 200 in place, the physician can perform several diagnostic and therapeutic procedures with only one cannulation of the common bile duct.

The present invention has been described with reference to the attached Figures and described embodiments. It is to be appreciated that other embodiments may fulfill the spirit and scope of the present invention and that the true nature and scope of the present invention is to be determined with reference to the claims appended hereto.

We claim:

1. A method of electrosurgically obtaining access to the biliary tree of a patient and visualizing a duct thereof using a catheter having at least a first lumen and a second lumen defined therethrough, each lumen terminating in an opening defined at a distal end of said catheter, said first lumen of said catheter having a needle-knife disposed therein, said needle-knife having a distal end and being connected to a deployment means at a proximal end of said catheter for extending and retracting said needle-knife between a deployed position and a fully sheathed position relative to said distal end of said catheter, said deployment means having adjustable stop means for adjusting the distance between said distal end of said needle-knife and said distal end of said catheter, said needle-knife electrically communicating with a power source, said method comprising the steps of:

inserting said catheter and said needle-knife in said sheathed position through an endoscope and into the duodenum of the patient proximal to the entrance to the common bile duct;

deploying said needle-knife from said sheathed position relative to said distal end of said catheter and positioning said distal end of said needle-knife relative to said distal end of said catheter by manipulating said adjustable stop means;

manipulating said needle-knife and applying current thereto to incise tissue proximal to said entrance to said common bile duct;

withdrawing said needle-knife into said sheathed position relative to said distal end of said catheter;

advancing said catheter into said common bile duct to a desired location within said duct; and infusing a contrast medium through said second lumen of said catheter to visualize said common bile duct through the use of said contrast medium while said needle-knife remains in said first lumen of said catheter.

2. The method of claim 1, further comprising the step of withdrawing said needle-knife through said first lumen of said catheter and then threading a wire guide through said first lumen of said catheter while said catheter remains in said common bile duct.

3. The method of claim 2, further comprising the steps of:

advancing said wire guide through said opening defined in said distal end of said catheter and along said common bile duct;

further advancing said catheter along said wire guide to a second desired location within said common bile duct; and infusing said contrast medium through said second lumen of said catheter to visualize said duct while said wire guide remains in said first lumen of said catheter.

4. A method of electrosurgically obtaining access to a duct of a patient using a catheter having at least a first lumen and a second lumen defined therethrough, each lumen terminating in an opening defined at a distal end of said catheter, said first lumen of said catheter having an elongated sheath threaded therethrough, said sheath having a needle-knife disposed therein, said needle-knife having a distal end and being connected to a deployment means at a proximal end of said sheath for extending and retracting said needle-knife between a fully deployed position and a sheathed position relative to a distal end of said sheath, said deployment means having adjustable stop means for adjusting the distance between said distal end of said needle-knife and said distal end of said catheter, said needle-knife electrically communicating with a power source, said method comprising:

- inserting said catheter containing said needle-knife and said sheath through an endoscope and into a position proximal to an entrance to a duct of the patient;
- deploying said needle-knife from said sheathed position relative to said distal end of said sheath and positioning said distal end of said needle-knife relative to said distal end of said catheter by manipulating said adjustable stop means;
- manipulating said needle-knife and applying current thereto to incise tissue proximal to said entrance to said duct;
- withdrawing said needle-knife into said sheathed position relative to said distal end of said sheath while said sheath remains in said first lumen of said catheter;
- advancing said catheter into said duct to a desired location within said duct while said sheath remains in said first lumen of said catheter; and
- infusing a contrast medium through said second lumen of said catheter to visualize said duct while said sheath and said needle-knife remain in said first lumen of said catheter.

5. The method of claim 4, further comprising the step of withdrawing said sheath and said needle-knife through said first lumen of said catheter and then threading a wire guide through said first lumen of said catheter while said catheter remains in said duct.

6. The method of claim 5, further comprising the steps of:

- advancing said wire guide through said opening defined in said distal end of said catheter and along said duct;
- further advancing said catheter along said wire guide to a second desired location within said duct; and
- infusing said contrast medium through said second lumen of said catheter to visualize said duct while said wire guide remains in said first lumen of said catheter.

7. A method of electrosurgically obtaining access to a duct of a patient using a catheter having at least a first lumen and a second lumen defined therethrough, each lumen terminating in an opening defined at a distal end of said catheter, said first lumen of said catheter having an elongated sheath threaded therethrough, said sheath having a needle-knife disposed therein, said needle-knife having a distal end and being connected to a deployment means at a proximal end of said sheath for extending and retracting said needle-knife between a fully deployed position and a sheathed position relative to a distal end of said sheath, said deployment means having adjustable stop means for adjusting the distance between said distal end of said needle-knife and said distal end of said catheter, said needle-knife electrically communicating with a power source, said method comprising:

- inserting said catheter containing said needle-knife and said sheath through an endoscope and into a position proximal to an entrance to a duct of the patient;
- deploying said needle-knife from said sheathed position relative to said distal end of said sheath and positioning said distal end of said needle-knife relative to said distal end of said catheter by manipulating said adjustable stop means;
- manipulating said needle-knife and applying current thereto to incise tissue proximal to said entrance to said duct;
- withdrawing said sheath and said needle-knife through said first lumen of said catheter and then threading a wire guide through said first lumen of said catheter while said catheter remains in said position proximal to said entrance of said duct;
- advancing said wire guide through said opening defined in said distal end of said catheter and along said duct;
- advancing said catheter over said wire guide to a desired location within said duct; and
- infusing a contrast medium through said second lumen of said catheter to visualize said duct while said wire guide remains in said first lumen of said catheter.

* * * * *